(12) United States Patent
Golberg et al.

(10) Patent No.: US 11,078,474 B2
(45) Date of Patent: Aug. 3, 2021

(54) METHOD AND DEVICE FOR NON-THERMAL EXTRACTION OF PHYTOCHEMICALS FROM MACROALGAE

(71) Applicant: RAMOT AT TEL-AVIV UNIVERSITY LTD., Tel Aviv (IL)

(72) Inventors: Alexander Golberg, Tel Aviv (IL); Arthur Robin, Tel Aviv (IL)

(73) Assignee: Ramot at Tel-Aviv University Ltd., Tel Aviv (IL)

(*) Notice: Subject to any disclaimer, the term of this patent is extended or adjusted under 35 U.S.C. 154(b) by 0 days.

(21) Appl. No.: 15/884,114

(22) Filed: Jan. 30, 2018

(65) Prior Publication Data

US 2018/0223272 A1   Aug. 9, 2018

Related U.S. Application Data

(63) Continuation-in-part of application No. PCT/IL2016/051202, filed on Nov. 7, 2016.

(60) Provisional application No. 62/252,723, filed on Nov. 9, 2015.

(51) Int. Cl.
```
A61K 36/02    (2006.01)
C12N 13/00    (2006.01)
C07K 1/36     (2006.01)
C07K 4/08     (2006.01)
C07K 1/24     (2006.01)
C07K 1/22     (2006.01)
B01D 11/02    (2006.01)
C07K 1/12     (2006.01)
C07K 14/405   (2006.01)
C12M 1/00     (2006.01)
B01D 15/08    (2006.01)
```
(52) U.S. Cl.
CPC .......... *C12N 13/00* (2013.01); *B01D 11/0211* (2013.01); *B01D 11/0257* (2013.01); *C07K 1/12* (2013.01); *C07K 1/22* (2013.01); *C07K 1/24* (2013.01); *C07K 1/36* (2013.01); *C07K 4/08* (2013.01); *C07K 14/405* (2013.01); *C12M 47/06* (2013.01); *B01D 11/0207* (2013.01); *B01D 15/08* (2013.01)

(58) Field of Classification Search
None
See application file for complete search history.

(56) References Cited

U.S. PATENT DOCUMENTS

| | | |
|---|---|---|
| 2003/0061518 A1 | 3/2003 | Yamaguchi et al. |
| 2010/0233761 A1* | 9/2010 | Czartoski .......... C12N 1/06 435/71.1 |
| 2011/0107655 A1 | 5/2011 | Kempkes et al. |
| 2012/0040428 A1 | 2/2012 | Reep et al. |

FOREIGN PATENT DOCUMENTS

| | | |
|---|---|---|
| WO | 2008034228 A1 | 3/2008 |
| WO | 2009042501 A1 | 4/2009 |
| WO | 2012010969 A2 | 1/2012 |

OTHER PUBLICATIONS

Revilla et al. (1998) J. Agric. Food Chem. 46: 4592-4597. (Year: 1998).*
Raskin et al. (2004) Current Pharmaceutical Design, 10: 3419-3429. (Year: 2004).*
Polikovsky et al; "In silico food allergenic risk evaluation of proteins extracted from macroalgae *Ulva* sp. with pulsed electric fields" Food Chemistry 276 pp. 735-744. (2019).
Postma et al; "Biorefinery of the macroalgae Ulva lactuca: extraction of proteins and carbohydrates by mild disintegration" Journal of Applied Phycology 30(2) pp. 1281-1293. (2018).
Rubin et al; "Functional Protein Concentrates Extracted from the Green Marine Macroalga *Ulva* sp., by High Voltage Pulsed Electric Fields and Mechanical Press" ACS Sustainable Chem. Eng.Jun. 11, 2018. pp. 13696-13705/ (2018).
Extended European Search Report (EESR) received in EP Application No. EP16863778.3, dated Jun. 5, 2019.
Polikovsky, M., Fernand, F., Sack, M., Frey, W., M?ller, G., & Golberg, A. (2016). Towards marine biorefineries: Selective proteins extractions from marine macroalgae Ulva with pulsed electric fields. Innovative Food Science & Emerging Technologies, vol. 37, pp. 194-200.(2016).
Lebovka, Farid, Nikolai Vorobiev, and Eugene Chemat. "Enhancing extraction processes in the food industry". CRC Press, (2011).
Postma, R., Eppink, M., Barbosa, M., Brandenburg, W., & Wijffels, R. "Proteins from micro- and macro-algae". In Symposium Biorefinery for Food, Fuel and Materials, p. 151. (2013).
Yarmush ML, Golberg A, Serša G, Kotnik T, Miklavčič D. Electroporation-based technologies for medicine: principles, applications, and challenges. Annu. Rev. Biomed. Eng., 16, pp. 295-320. (2014).
Barbarino E, Lourenço SO. An evaluation of methods for extraction and quantification of protein from marine macro- and microalgae. J. Appl. Phycol., 17(5), pp. 447-460. (2005).
Bluhm H, Sack M. Industrial-scale treatment of biological tissue with pulsed electric fields. in Electrotechnologies for Extraction from Food Plants and Biomaterial, E. Vorobiev and N Lebovka Eds. Springer Science and Business Media LLC, pp. 237-269. (2008).
Carey DE, Yang Y, McNamara PJ, Mayer BK, Recovery of agricultural nutrients from biorefineries. Bioresource Technology, 215, pp. 186-198 . (2016).
Chen WT, Ma J, Zhang Y, Gai C, Qian W, Physical pretreatments of wastewater algae to reduce ash content and improve thermal decomposition characteristics. Bioresource Technology, 169, pp. 816-820. (2014).
Coustets M, Joubert-Durigneux V, Hérault J, Schoefs B, Blanckaert V, Garnier J.-P, Teissié J. Optimization of protein electroextraction from microalgae by a flow process. Bioelectrochemistry, , 103, pp. 74-81. (2015).

(Continued)

*Primary Examiner* — Russell G Fiebig
(74) *Attorney, Agent, or Firm* — Knobbe, Martens, Olson & Bear LLP

(57) ABSTRACT

A method is for the extraction of a phytochemical, e.g., peptide or protein, or a chemical element from a macroalgae, by applying pulsed electric field (PEF)- or continuous electric field (CEF)-treatment to the macroalgae in a solvent, under pressure higher than the ambient pressure. A device and system carry out this method.

13 Claims, 12 Drawing Sheets

(56) References Cited

OTHER PUBLICATIONS

Evans FD, Critchley AT, Seaweeds for animal production use. Journal of Applied Phycology, 26(2), pp. 891-899. (2014).

Fleurence J, Le Coeur C, Mabeau S, Maurice M, Landrein A. Comparison of different extractive procedures for proteins from the edible seaweeds *Ulva rigida* and *Ulva rotundata*. J. Appl. Phycol., 7(6), pp. 577-582. (1995).

Galland-Irmouli AV, Pons L, Luçon M, Villaume C, Mrabet NT, Guéant JL, Fleurence J. One-step purification of R-phycoerythrin from the red macroalga Palmaria palmata using preparative polyacrylamide gel electrophoresis. Journal of Chromatography B: Biomedical Sciences and Applications, 739(1), pp. 117-123. (2000).

Ganeva V, Galutzov B. Electropulsation as an alternative method for protein extraction from yeast. FEMS Microbiol. Lett., 174(2), pp. 279-284. (1999).

Ganeva V, Galutzov B, Teissié J. High yield electroextraction of proteins from yeast by a flow process, Anal. Biochem., 315(1), pp. 77-84. (2003).

Goettel M, Eing C, Gusbeth C, Straessner R, Frey W. Pulsed electric field assisted extraction of intracellular valuables from microalgae. Algal Res., 2(4), pp. 401-408. (2013).

Golberg A, Rubinsky B. The effect of electroporation type pulsed electric fields on DNA in aqueous solution, Technol. Cancer Res. Treat., 9(4), pp. 423-430. (2010).

Golberg A, Broelsch GF, Bohr S, Mihm MC, Austen WG, Albadawi H, Watkins MT, Yarmush ML. Non-thermal, pulsed electric field cell ablation: A novel tool for regenerative medicine and scarless skin regeneration. Technology, 1(1), pp. 1-8. (2013).

Golberg A, Sack M, Teissie J, Pataro G, Pliquett U, Saulis G, Stefan T, Miklavcic D, Vorobiev E, Frey W, Energy-efficient biomass processing with pulsed electric fields for bioeconomy and sustainable development. Biotechnology for biofuels, 9(1), 94. (2016).

Haberl S, Miklavcic D, Sersa G, Frey W, Rubinsky B, Cell membrane electroporation—Part 2: the applications (2013).

Haberl Meglic S, Marolt T, Miklavcic D. Protein extraction by means of electroporation from *E. coli* with preserved viability. J. Membr. Biol., (2015).

Harnedy PA, FitzGerald RJ. Extraction of protein from the macroalga Palmaria palmate. LWT—Food Sci. Technol., 51(1), pp. 375-382. (2013).

He Y, Fang Z, Zhang J, Li X, Bao J, De-ashing treatment of corn stover improves the efficiencies of enzymatic hydrolysis and consequent ethanol fermentation. Bioresource Technology, 169, pp. 552-558. (2013).

Hu Y, Wang S, Wang Q, He Z, Lin X, Xu S, Ji H, Li Y, Effect of different pretreatments on the thermal degradation of seaweed biomass. Proceedings of the Combustion Institute, 36(2), pp. 2271-2281. (2017).

Huang C, Wu X, Huang Y, Lai C, Li X, Yong Q, Prewashing enhances the liquid hot water pretreatment efficiency of waste wheat straw with high free ash content. Bioresource Technology, 219, pp. 583-588. (2016).

Joubert Y, Fleurence J. Simultaneous extraction of proteins and DNA by an enzymatic treatment of the cell wall of Palmaria palmata (Rhodophyta). J. Appl. Phycol., 20(1), pp. 55-61. (2007).

Kang L, Wei W, Pallapolu VR, Lee YY, Enhanced ethanol production from de-ashed paper sludge by simultaneous saccharification and fermentation and simultaneous saccharification and cofermentation. BioResources, 6(4), pp. 3791-3808. (2011).

Kotnik T, Kramar P, Pucihar G, Miklavcic D, Tarek M, Cell membrane electroporation—Part 1: The phenomenon. IEEE Electrical Insulation Magazine, 28(5), pp. 14-23. (2012).

Kotnik T, Frey W, Sack M, Haberl Meglič S, Peterka M, Miklavčič D. Electroporation-based applications in biotechnology, Trends Biotechnol., 33(8), pp. 480-488. (2015).

Mahnič-Kalamiza S, Vorobiev E, Miklavčič D, Electroporation in food processing and biorefinery. The Journal of Membrane Biology, 247(12), 1pp. 279-1304. (2014).

Makkar HPS, Tran G, Heuzé V, Giger-Reverdin S, Lessire M, Lebas F, Ankers P. Seaweeds for livestock diets: A review. Animal Feed Science and Technology, 212, pp. 1-17. (2016).

Ohshima T, Tamura T, Sato M. Influence of pulsed electric field on various enzyme activities. J. Electrostat., 65(3), pp. 156-161. (2007).

Parniakov O, Barba FJ, Grimi N, Marchal L, Jubeau S, Lebovka N, Vorobiev E. Pulsed electric field and pH assisted selective extraction of intracellular components from microalgae Nannochloropsis, Algal Res., 8, pp. 128-134. (2015).

Pattiya A, Chaow-u-thai A, Rittidech S, The Influence of pretreatment techniques on ash content of cassava residues. International Journal of Green Energy, 10(5), pp. 544-552. (2013).

Polikovsky M, Fernand F, Sack M, Frey W, Müller G, Golberg A, Towards marine biorefineries: Selective proteins extractions from marine macroalgae Ulva with pulsed electric fields. Innovative Food Science & Emerging Technologies. (2016).

Raso J, Frey W, Ferrari G, Pataro G, Knorr D, Teissie J, Miklavčič D, Recommendations guidelines on the key information to be reported in studies of application of PEF technology in food and biotechnological processes. Innovative Food Science & Emerging Technologies, 37, pp. 312-321. (2016).

Rouxel C, Daniel A, Jérôme M, Etienne M, Fleurence J. Species identification by SDS-PAGE of red algae used as seafood or a food ingredient. Food Chem., 74(3), 349-353. (2001).

Rubinsky B. Irreversible electroporation in medicine. Technology in Cancer Research & Treatment, 2007, 6(4), 255-260.

Sack M, Eing C, Berghöfer T, Buth L, Stängle R, Frey W, Bluhm H. Electroporation-assisted dewatering as an alternative method for drying plants. IEEE Transactions on Plasma Science, 36(5 PART 3), pp. 2577-2585. (2008).

Sack M, Bluhm H, New measurement methods for an industrial-scale electroporation facility for sugar beets. IEEE Trans. Ind. Appl., 44(4), pp. 1074-1083. (2008).

Sack M, Attmann F, Stängle R, Wolf A, Frey W, Müller G. Upgrade of the electroporation device KEA-MOBIL. Acta Phys. Pol. A, 115(6), pp. 1081-1083. (2009).

Sack M, Sigler J, Eing C, Stukenbrock L, Stängle R, Wolf A, Müller G. Operation of an electroporation device for grape mash. IEEE Transactions on Plasma Science, 38(8), 1 pp. 928-1934. (2010a).

Sack M, Sigler J, Frenzel S, Eing C, Arnold J, Michelberger T, Frey W, Attmann F, Stukenbrock L, Müller G. Research on industrial-scale electroporation devices fostering the extraction of substances from biological tissue. Food Eng. Rev., 2(2), 1 pp. 47-156. (2010b).

Stefanidis SD, Heracleous E, Patiaka DT, Kalogiannis KG, Michailof CM, Lappas AA, Optimization of bio-oil yields by demineralization of low quality biomass. Biomass and Bioenergy, 83, pp. 105-115. (2015).

Vorobiev E, Lebovka N, Enhanced extraction from solid foods and biosuspensions by pulsed electrical energy. Food Eng. Rev., 2(2), pp. 95-108. (2010).

Wong K, Chikeung Cheung P. Influence of drying treatment on three *Sargassum* species 2. Protein extractability, in vitro protein digestibility and amino acid profile of protein concentrates. J. Appl. Phycol., 13(1), pp. 51-58. (2001).

Vanthoor-Koopmans et al., Biorefinery of microaigae for food and fuel. Bioresource technology, 135, pp. 142-149. (2016). (Abstract only).

International Search Report and Written Opinion received in PCT Application No. PCT/IL2016/051202, dated Mar. 1, 2017.

Vandanjon, L.; Vallet, L.; Le Glatin, T.; Deleris, P.; Baron, R.; Bourseau, P.; Dumay, J., Valorization of the macroalga *Sargassum muticum* by enzymatic hydrolysis. Interest of surfactants to improve the extraction of phlorotannins and polysaccharides. *Journal of Marine Biology and Aquaculture* (Ommega Online Publishers), 2016, 2(1), 1-7.

Sudhakar, M.P.; Jagatheesan, A.; Perumal, K.; Arunkumar, K., Methods of phycobiliprotein extraction from *Gracilaria crassa* and its applications in food colourants. *Algal Res.* 2015, 8, 115-120.

* cited by examiner

METHOD AND DEVICE FOR NON-THERMAL EXTRACTION OF PHYTOCHEMICALS FROM MACROALGAE

CROSS-REFERENCE TO RELATED APPLICATIONS

The present application is a continuation-in-part of International Application No. PCT/IL2016/051202, filed Nov. 7, 2016, designating the U.S., and published as WO 2017/081677 on May 18, 2017, which claims the benefit of U.S. Provisional Patent Application No. 62/252,723, filed Nov. 9, 2015. Any and all applications for which a foreign or domestic priority claim is identified above and/or in the Application Data Sheet as filed with the present application are hereby incorporated by reference under 37 CFR 1.57, the entire contents of each and all these applications being herewith incorporated by reference in their entirety as if fully disclosed herein.

TECHNICAL FIELD

The present invention relates to a method for the extraction of a phytochemical, e.g., a peptide or protein, or a chemical element from a macroalgae; and to a device for carrying out said method.

BACKGROUND ART

Global population growth combined with the increase in quality of life in the era of changing climate will increase the demand for food, chemicals and fuels in general, and for plant proteins in particular. Considering the positive impact of plant proteins consumption on sustainability and reduction of land, water, fertilizers and energy consumption, there is a consciously growing interest in exploring different plant sources for direct proteins use in the diet, either directly as entire plant or combined in the processed food products (Tuso et al., 2013). In the last five decades microalgae biomass gained a lot of interest as a feedstock for proteins production. More recently food proteins production is considered as a valuable co-product with biofuels in the algal biorefineries. The production of microalgae biomass, however, is still cost prohibitive and further advances in the cultivation and harvesting technologies are required. Macroalgae, large multicellular organisms, have been mostly overlooked as a feedstock for protein production for many years. However, many of the marine red and green macroalgae species have shown significantly higher content of proteins in comparison to the terrestrial plant proteins sources such as soy, nuts, and cereals (Fleurence, 2004; Harnedy and FitzGerald, 2011). In addition to their high yields and nutritional properties, marine algae derived proteins and peptides have shown additional value because of their nutraceutical, pharmaceutical and cosmeceutical properties such as antioxidant, antihypertensive, immune-modulatory, anticoagulant and hepeto-protective substances (Fleurence, 2004; Harnedy and FitzGerald, 2011).

The value of the macroalgae as a protein source depends on the extracted protein yields and the ability to preserve its functional properties. The complex, viscous and often charged macroalgae cell wall and extracellular matrix make the extraction process challenging (Joubert and Fleurence, 2007). Osmotic shock, mechanical grinding, high shear force, ultrasonic treatment, acid and alkaline pretreatment and polysaccharidase aided digestion, and their combination have been used to increase the extraction yields (Barbarino and Lourenço, 2005; Wong and Chikeung Cheung, 2001; Rouxel et al., 2001; Galland-Irmouli et al., 2000; Fleurence et al., 1995; Harnedy and FitzGerald, 2013). Although the mentioned methods were shown to increase the extraction yields, they involve either thermal or chemical procedures that could affect the functionality of the extracted proteins and peptides.

Pulsed electric field (PEF) is an emerging, non-thermal food processing technology already used for energy-efficient extraction of proteins from microalgae. Although the exact mechanism of biological tissue permeabilisation by PEF is not fully understood, PEF technology is currently used in multiple applications in medicine and biotechnology (Kotnik et al., 2015; Rubinsky, 2007; Yarmush et al., 2014). The current theory suggests that the membrane permeabilisation is achieved through the formation of aqueous pores on the cell membrane, a phenomenon known as electroporation (Weaver and Chizmadzhev, 1996).

SUMMARY OF INVENTION

It has now been found, in accordance with the present invention, that phytochemicals such as proteins may be efficiently extracted from macroalgae, while preserving their chemical structure and functional properties, by a non-thermal PEF treatment, carried out under pressure higher than ambient pressure, which causes to cell membrane rupture due to irreversible electroporation. Such a process can be carried out continuously, e.g., in a fluidized bed chamber, which further allows for direct separation of the extracted product, cutting the costs of downstream purification.

In a further study described herein it has been found that PEF also enhances deashing of biomass from a high ash content green marine macroalga, using hydraulic pressing. In particular, by inducing cell permeabilization of the fresh biomass, PEF was able to enhance the ash extraction from 18.4% (non-treated control) to 37.4% of the total ash content in average, significantly enhancing the extraction of five of the major ash elements (K, Mg, Na, P and S) compared to pressing alone.

In one aspect, the present invention thus relates to a method for the extraction of a phytochemical from a macroalgae, said method comprising applying pulsed electric field (PEF)- or continuous electric field (CEF)-treatment, preferably non-thermal PEF- or CEF treatment, to said macroalgae in a solvent, under pressure higher than the ambient pressure, thereby extracting said phytochemical from said macroalgae cells into said solvent.

In another aspect, the present invention relates to a macroalgae phytochemical, e.g., a peptide, protein, sugar, or small molecule, obtained by the method defined above.

In yet another aspect, the present invention provides a device for the extraction of a phytochemical from a macroalgae, said device comprising: (i) a PEF- or CEF-treatment chamber comprising at least one inlet and at least one outlet; (ii) a first electrode and a second electrode positioned for creating an electric field in said treatment chamber; (iii) optionally a pressure generating mean for generating pressure within said treatment chamber; (iv) optionally, an agitator and/or air bubbling unit for agitating and mixing the content of said treatment chamber; and (v) optionally, a filtering unit located at the outlet, wherein upon introducing said macroalgae in a solvent into said treatment chamber, and applying PEF- or CEF treatment to said solvent under pressure higher than the ambient pressure, said phytochemical is extracted from said macroalgae into said solvent.

In still another aspect, the present invention provides a system for the extraction and separation of a phytochemical from a macroalgae, said system comprising: (i) a device as defined above, for the extraction of said phytochemical from said macroalgae into said solvent; and (ii) a separation unit comprising at least one inlet and at least one outlet, for separating said phytochemical from said solvent, wherein upon extracting said phytochemical from said macroalgae into said solvent, said solvent is optionally filtered for removal of macroalgae debris; and said phytochemical is then separated from said solvent in said separation unit.

In a further aspect, the present invention relates to a method for deashing a cell biomass, e.g., a plant biomass such as seaweed biomass, by applying PEF- or CEF-treatment to said cell biomass in a solvent, preferably non-thermal PEF or CEF treatment, more preferably non-thermal PEF treatment, optionally under pressure higher than the ambient pressure, thereby extracting ash fraction from said cell biomass into said solvent. More particularly, the invention relates to a method for improving a cell biomass, said method comprising deashing, i.e., extracting ash fraction from, said cell biomass by applying PEF- or CEF-treatment, preferably non-thermal PEF or CEF treatment, more preferably non-thermal PEF treatment, to said cell biomass in a solvent, optionally under pressure higher than the ambient pressure. In certain embodiments, the improved biomass (e.g., plant biomass such as seaweed biomass) can be used as a feedstock.

The ash fraction extracted from the cell biomass by this method may comprise a chemical element such as phosphorus or a metal. In still a further aspect, the present invention thus relates to a method for extraction of a chemical element from a cell biomass, said method comprising applying PEF- or CEF-treatment, preferably non-thermal PEF or CEF treatment, more preferably non-thermal PEF treatment, to said cell biomass in a solvent, optionally under pressure higher than the ambient pressure, thereby extracting said chemical element from said cell biomass into said solvent.

DETAILED DESCRIPTION

Figure 1:
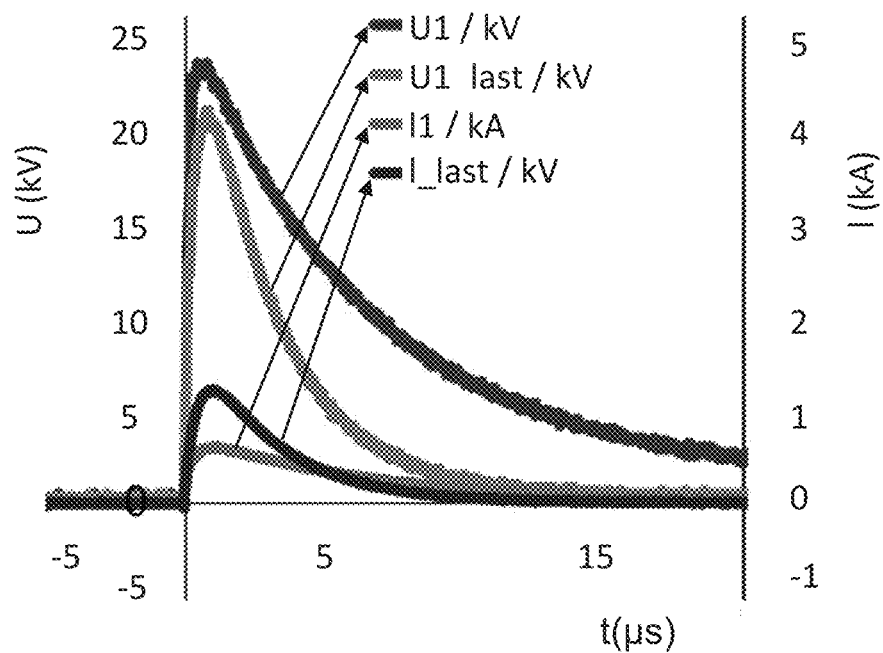
FIG. 1 shows shape and magnitude of the single electric pulse delivered for macroalgae biomass electroporation. The shape for actually delivered voltage and measured current is shown for the first and last pulse in the series of 75 pulses applied on the biomass.

In one aspect, the present invention relates to a method, i.e., process, for the extraction of at least one phytochemical from a macroalgae, said method comprising applying PEF or CEF treatment, preferably non-thermal PEF or CEF treatment, to said macroalgae in a solvent, under pressure higher than the ambient pressure, thereby extracting said at least one phytochemical from said macroalgae cells into said solvent.

The term "macroalgae" as used herein refer to a macrophyte, i.e., a macroscopic, multicellular (as opposed to microalgae) aquatic plant that grows in or near water and is emergent, submergent, or floating. Generally, macroalgae are divided to three groups known as the green algae, red algae, and brown algae, each one being further divided to families, genus, and species. The macroalgae treated according to the method of the invention may be in the natural form, i.e., a wet macroalgae, or as a dried or semidried material obtained after dehydrating said macroalgae, e.g., in an oven, and optionally cutting and/or grinding.

A list of macroalgae that may be treated according to the method of the present invention can be found, e.g., in AlgaeBase (a database of information on algae that includes terrestrial, marine and freshwater organisms; http://www.algaebase.org/). In particular embodiments, the macroalgae being treated according to the method of the invention is a green macroalgae, e.g., *Ulva lactuca*, which belongs to the genus *Ulva*, also known by the name sea lettuce. In other particular embodiments, the macroalgae being treated according to the method of the invention is a red macroalgae, e.g., of the genus *Porphyra, Kapaphycaus, Gelidium, Gracilaria*, or *Chondrus*; or a brown algae, e.g., of the genus *Hizikia* or *Laminaria* (e.g., *Laminaria japonica*).

PEF treatment is a process consisting of applying short microsecond pulses of high voltage at high frequency, leading to biological tissue permeabilization (Kotnik et al., 2012). The term "pulsed electric field (PEF) treatment" thus refers to the application of a pulsed electric field characterized by specific voltage, electric field strength, pulse duration, number of pulses, and pulses frequency. Although the exact mechanism of biological tissue permeabilization by PEF is not fully understood, the current theory suggests that the membrane permeabilization is achieved through the formation of aqueous pores on the cell membrane, a phenomenon known as electroporation.

The term "continuous electric field (CEF) treatment" refers to the application of a single long pulse, e.g., a direct current (DC).

In certain embodiments, the PEF or CEF treatment applied according to the method of the present invention is homogeneously distributed in said solvent.

In certain embodiments, the PEF or CEF treatment applied according to the method of the present invention electroporates the cells of the treated macroalgae thereby causing extraction of said phytochemical from said macroalgae cells into the solvent. More particularly, the PEF or CEF treatment applied causes both opening of the membrane of said macroalgae cells and configuration changes in the extracellular matrix of said macroalgae, thereby enabling said extraction of said phytochemical from said macroalgae cells into said solvent.

In certain embodiments, the method of the present invention comprises applying CEF treatment to said macroalgae in said solvent, under pressure as defined above. In particular such embodiments, said method comprises applying DC previously known as galvanic current, i.e., a unidirectional flow of electric charge. The CEF treatment applied may be characterized by at least one of: (i) electric field strength of from about 10 to about 500 Volt, e.g., from about 10 to about 20 Volt, from about 20 to about 30 Volt, from about 30 to about 40 Volt, about 40 to about 50 Volt, from about 50 to about 60 Volt, from about 60 to about 70 Volt, from about 70 to about 80 Volt, from about 80 to about 90 Volt, from about 90 to about 100 Volt, from about 100 to about 200 Volt, from about 30 to about 300 Volt, from about 300 to about 400 Volt, or from about 400 to about 500 Volt; and pulse duration of from about 1 sec to about 10 min, e.g., from about 1 sec to about 10 sec, from about 10 sec to about 20 sec, from about 20 sec to about 30 sec, from about 30 sec to about 40 sec, from about 40 sec to about 50 sec, from about 50 sec to about 1 min, from about 1 min to about 2 min, from about 2 min to about 3 min, from about 3 min to about 4 min, from about 4 min to about 5 min, from about 5 min to about 6 min, from about 6 min to about 7 min, from about 7 min to about 8 min, from about 8 min to about 9 min, or from about 9 min to about 10 min.

In certain embodiments, the method of the present invention comprises applying PEF treatment to said macroalgae in said solvent, under pressure as defined above. In particular such embodiments, the PEF treatment applied is characterized by at least one of: (i) pulse number of from 1 to about 10,000, e.g., from 1 to about 500, from 500 to about 1000, from about 1000 to about 2000, from about 2000 to about 3000, from about 2000 to about 4000, from about 4000 to about 5000, from about 5000 to about 6000, from about 6000 to about 7000, from about 7000 to about 8000, from about 8000 to about 9000, or from about 9000 to about 10000; (ii) pulse duration of from about 50 ns to about 10 ms, e.g., from about 50 ns to about 500 ns, from about 500 ns to about 1 ms, from about 1 ms to about 2 ms, from about 2 ms to about 3 ms, from about 3 ms to about 4 ms, from about 4 ms to about 5 ms, from about 5 ms to about 6 ms, from about 6 ms to about 7 ms, from about 7 ms to about 8 ms, from about 8 ms to about 9 ms, or from about 9 ms to about 10 ms; (iii) electric field strength of about 0.1 to about 100 kV/cm, e.g., about 0.1 to about 0.5 kV/cm, about 0.5 to about 1 kV/cm, about 1 to about 5 kV/cm, about 5 to about 10 kV/cm, about 10 to about 20 kV/cm, about 20 to about 30 kV/cm, about 30 to about 40 kV/cm, about 40 to about 50 kV/cm, about 50 to about 60 kV/cm, about 60 to about 70 kV/cm, about 70 to about 80 kV/cm, about 80 to about 90 kV/cm, or about 90 to about 100 kV/cm; and (iv) pulse frequency of from 0.1 to about 10000 Hz, e.g., from 0.1 to about 10 Hz, from 10 to about 100 Hz, from 100 to about 500 Hz, from 500 to about 1000 Hz, from 1000 to about 2000 Hz, from 2000 to about 3000 Hz, from 3000 to about 4000 Hz, from 4000 to about 5000 Hz, from 5000 to about 6000 Hz, from 6000 to about 7000 Hz, from 7000 to about 8000 Hz, from 8000 to about 9000 Hz, or from 9000 to about 10000 Hz.

As would be clear to any person skilled in the art, the particular characteristics (properties) of the PEF treatment applied, i.e., the combination of particular pulse number, pulse duration, electric field strength and pulse frequency selected, may affect the efficiency of the process, e.g., the electroporation efficiency, and moreover, the temperature developed in the solvent exposed to said PEF treatment. The particular characteristics of the PEF treatment applied should thus be selected such that the extraction process, in terms of yield, would be as efficient as possible, and the solvent's temperature developed during and as a result of said PEF treatment would not be detrimental to said phytochemical. In particular embodiments, the properties of the PEF treatment applied are selected such that the process carried out is considered "non-thermal process", i.e., the solvent's temperature developed during said PEF treatment does not exceed 90° C., e.g., in the range of 25° C.-90° C., 25° C.-70° C., 25° C.-60° C., 25° C.-50° C., or 25° C.-40° C. Such a non-thermal process might be of high importance in cases said phytochemical is a compound sensitive to relatively high temperatures such as a peptide or protein, or a combination thereof.

According to the present invention, the PEF or CEF treatment is applied under a pressure that is higher than the ambient pressure, i.e., simultaneously with said pressure. The term "ambient pressure" refers to the pressure of the medium surrounding the treatment zone, i.e., the zone (e.g., vessel or reactor) wherein said PEF or CEF treatment is carried out, and in certain cases actually denotes the standard atmospheric pressure (also referred to as the standard atmosphere, atm) that is 1013.25 millibars or 760 mmHg A pressure higher than the ambient pressure may thus be any pressure that is higher than the pressure which comes into contact with the treatment zone, e.g., any pressure within the range of about 1 atm to 10 atm or more. According to the invention, pressure can be applied using any technique known in the art, e.g., a mechanical press or centrifugation power. In certain embodiments, the pressure applied during said PEF or CEF treatment is constant during the whole of said treatment. In other embodiments, the pressure applied during said PEF or CEF treatment varies, and may either increase or decrease during said PEF or CEF treatment.

The solvent used according to the method of the present invention may be any suitable solvent, i.e., either an inorganic solvent such as fresh water, tap water, saline, or salt water (seawater); or an organic solvent such as, without limiting, acetic acid, acetone, acetonitrile, methanol, ethanol, propanol, isopropanol butanol, t-butyl alcohol, hexane, cyclohexane, chlorobenzene, chloroform, 1,2-dichloroethane, ethylene glycol, diethylene glycol, diethyl ether, ethyl acetate, methylene chloride, benzene, or a combination thereof. The solvent in which said macroalgae is submerged and treated may affect the efficiency of the treatment applied to said macroalgae, e.g., the extraction efficiency of said phytochemical from said macroalgae. In particular embodiments, said solvent is selected according to the phytochemical to be extracted. For example, for extraction of soluble peptides or proteins, water can be used as the solvent; and for extraction of phenols, a solvent such as ethanol can be used.

The method of the present invention may be used so as to extract any particular phytochemical or combination of phytochemicals from the macroalgae treated. Particular such phytochemicals include, e.g., peptides and proteins (including proteins that are naturally occurring in macroalgae as well as recombinant proteins), sugars, small molecules, and any combinations thereof. Phytochemicals occurring in macroalgae may be used, e.g., in the food industry, in the cosmetic industry, or for pharmaceutical purposes.

In certain embodiments such as those exemplified herein, the phytochemical extracted from said macroalgae is a peptide, protein, e.g., an active site-containing protein (i.e., a non-structural protein including, without being limited to, an antibody, protein antigen, enzyme, protein substrate or inhibitor, receptor, and lectin), or a combination thereof. In particular such embodiments, the treatment applied according to the method of the invention is non-thermal, i.e., the temperature of the solvent developed during said, PEF or CEF treatment is in the range of about 25° C. to about 90° C., preferably about 25° C. to about 50° C. or 40° C., such that said treatment does not affect the functional properties of the product(s) extracted, i.e., said peptide, protein or protein combination does not denature, and its functional properties are preserved.

In certain embodiments, the method of the present invention further comprises the step of filtering said solvent, after the PEF or CEF treatment, so as to remove macroalgae debris from said solvent. Filtration can be carried out by any technique known in the art, as long as it does not harm the phytochemical being dissolved in said solvent.

In certain embodiments, the present invention relates to a method as defined in any one of the embodiments above, for the extraction of a peptide or protein, e.g., an active site-containing protein, from a macroalgae, the method comprising applying non-thermal PEF treatment to said macroalgae in a solvent, under pressure higher than the ambient pressure, thereby extracting said peptide or protein from said macroalgae cells into said solvent. In certain particular such embodiments, the non-thermal PEF treatment applied is characterized by at least one of: (i) pulse number of from 1 to about 10,000; (ii) pulse duration of from about 50 ns to about 10 ms; (iii) electric field strength of from about 0.1 to about 100 kV/cm; and (iv) pulse frequency of from 0.1 to about 10000 Hz. In other particular such embodiments, the protein extracted by the method of the invention is an active site-containing protein, and the PEF treatment applied does not affect the functional properties of said active site-containing protein. In further particular such embodiments, the solvent in which said macroalgae is treated is fresh water, tap water, saline, or salt water (seawater).

In certain embodiments, the method of the present invention, according to any one of the embodiments defined above, further comprises a step of separating said phytochemical from said solvent. Such a separation may be carried out utilizing any procedure or technique known in the art. For example, separation of said phytochemical may be carried out by column chromatography/separation, i.e., passing the solvent containing said phytochemical, after said PEF or CEF treatment, through a separation column comprising binding means having affinity to said phytochemical, to thereby bind said phytochemical; optionally washing said column to remove unspecific bound molecules; and releasing said phytochemical from said binding means.

Alternatively, the separation may be carried out by introducing binding means having affinity to said phytochemical into said solvent either prior to or after said PEF or CEF treatment, to thereby bind said phytochemical upon extraction from said macroalgae cells; isolating said binding means after said PEF or CEF treatment; and optionally releasing said phytochemical therefrom. In certain embodiments, the binding means referred to herein have functional groups capable of reversibly interacting with functional groups of said phytochemical, thus trapping said phytochemical. In other embodiments, separation of said phytochemical is carried out by introducing binding means having affinity to said phytochemical into said solvent, and said binding means are in the form of beads. In particular embodiments, (i) said phytochemical is a peptide or protein, e.g., an active site-containing protein, and said binding means comprise antibodies to said peptide or protein; (ii) said phytochemical is an enzyme and said binding means comprise a substrate or inhibitor of said enzyme; (iii) said phytochemical is a small molecule and said binding means comprise ionic functional groups capable of interacting with ions of opposite charge of said phytochemical; or (iv) said phytochemical is a sugar and said binding means comprise a lectin.

The method of the present invention may be carried out within any suitable chamber, vessel or reactor. In certain embodiments, the method of the invention comprises the steps of: (i) introducing said macroalgae submerged in said solvent into a PEF- or CEF-treatment chamber; (ii) subjecting said macroalgae to a PEF- or CEF-treatment under pressure higher than the ambient pressure, thereby electroporating the cells of said macroalgae and consequently extracting said phytochemical from said macroalgae cells into said solvent; and (iii) optionally filtering said solvent to remove macroalgae debris therefrom.

In one particular such embodiment, said PEF- or CEF-treatment chamber is a fluidized bed chamber. Such a method may further comprise introducing binding means, e.g., in the form of beads, having affinity to said phytochemical, into said solvent either prior to or after step (ii), to thereby bind said phytochemical upon extraction from said macroalgae cells; isolating said binding means from said solvent; and optionally releasing said phytochemical therefrom. Alternatively, such a method may further comprise passing said solvent, after said PEF- or CEF-treatment, through a separation column comprising binding means having affinity to said phytochemical, to thereby bind said phytochemical; optionally washing said column to remove unspecific bound molecules; and releasing said phytochemical from said binding means.

In another particular such embodiment, said PEF- or CEF-treatment chamber is a centrifugal chamber. In such a method, the pressure inside the treatment chamber that is required so as to extract said phytochemical from said macroalgae into said solvent, i.e., a pressure higher than the ambient pressure, in fact results from the centrifugal force created by the rotation of said centrifugal chamber during said PEF- or CEF-treatment, and the solvent (more specifically part of the solvent) containing the extracted phytochemical is continuously separated during the process as a result of said centrifugal force.

In another aspect, the present invention relates to a macroalgae phytochemical obtained by the method of the present invention as defined in any one of the embodiments above. The macroalgae phytochemical of the invention may be a peptide, protein, sugar, small molecule, or a combination thereof. In certain embodiments, said phytochemical is a peptide or protein, e.g., an active site-containing protein such as an antibody, protein antigen, enzyme, protein substrate or inhibitor, receptor, and lectin. Considering the characteristics of the process by which the phytochemical, e.g., peptide or protein, is obtained, said phytochemical is expected to be in its natural form, i.e., in the form it exists within the macroalgae cells.

In yet another aspect, the present invention provides a device for the extraction of a phytochemical from a macroalgae, said device comprising: (i) a PEF- or CEF-treatment chamber comprising at least one inlet and at least one outlet; (ii) a first electrode and a second electrode positioned for creating an electric field in said treatment chamber; (iii) optionally a pressure generating mean for generating pressure within said treatment chamber; (iv) optionally, an agitator and/or air bubbling unit for agitating and mixing the content of said treatment chamber; and (v) optionally, a filtering unit located at the outlet, wherein upon introducing said macroalgae in a solvent into said treatment chamber, and applying PEF- or CEF-treatment to said solvent under pressure higher than the ambient pressure, said phytochemical is extracted from said macroalgae into said solvent.

In certain embodiment, the device of the present invention comprises a CEF treatment chamber, and CEF treatment, e.g., constant DC, is applied under pressure higher than the ambient pressure. In other embodiment, the device of the invention comprises a PEF treatment chamber, and PEF treatment, more particularly non-thermal PEF treatment, is applied under pressure higher than the ambient pressure.

The device of the present invention comprises a first and second electrodes positioned for creating an electric field in said PEF- or CEF-treatment chamber. In particular embodiments, these electrodes are designed to provide different electric field at different locations of the electrodes, so as to save energy during said PEF- or CEF-treatment. In certain embodiments, both of said electrodes are positioned inside said treatment chamber. In other embodiments, one of said electrodes is positioned inside said treatment chamber, and the other one is positioned outside said treatment chamber. In further embodiments, both of said electrodes are positioned outside said treatment chamber. In yet another embodiment, said first and second electrodes are each constructed of a plurality of electrodes positioned such as to create an optimal electric field within said treatment chamber.

The device of the present invention as defined in any one of the embodiments above may further comprise a thermostat for measuring the temperature of said solvent during said PEF- or CEF-treatment; and a temperature controlling unit associated with said thermostat and capable of either (a) interrupting with said PEF- or CEF-treatment, and/or modulating one or more characteristics of said PEF- or CEF-treatment such as pulse number, pulse duration, electric field strength, pulse frequency, or any combination thereof; or (b) controlling the operation of external cooling means aimed at cooling said treatment chamber.

Such a temperature controlling unit might be of particular importance in cases PEF treatment, more particularly non-thermal PEF treatment, is applied, and is aimed at controlling the temperature developed during said PEF treatment from exceeding a particular threshold that might be detrimental to the product (phytochemical) extracted, i.e., keeping the solvent temperature in the range of 25° C.-90° C., 25° C.-70° C., 25° C.-60° C., 25° C.-50° C., or 25° C.-40° C. In cases wherein the solvent temperature constantly measured by the thermostat reaches a particular level, said temperature controlling unit may either interrupt with said PEF- or CEF-treatment, i.e., stop said PEF- or CEF-treatment for a particular time period, until the solvent temperature cools down; or modulate, i.e., alter, one or more of said PEF treatment, e.g., decrease pulse delivery frequency, so as to avoid further increase in the solvent temperature. Alternatively, such a temperature controlling unit may control the operation of external cooling means, which have no connection with the CEF- or PER-treatment and are aimed at cooling the treatment chamber thus reducing the temperature inside the treatment chamber.

In certain embodiments, the device of the present invention in any one of the embodiments defined above comprises said treatment chamber; said electrodes; said pressure generating mean; optionally said agitator and/or air bubbling unit; and optionally said filtering unit. In one particular such embodiment, the treatment chamber of said device is a fluidized bed chamber.

In other embodiments, the device of the present invention in any one of the embodiments defined above comprises said treatment chamber; said electrodes; and optionally said filtering unit. In one particular such embodiment, the treatment chamber of said device is a centrifugal chamber, wherein said pressure higher than the ambient pressure results from the centrifugal force created by the rotation of said centrifugal chamber during said PEF- or CEF-treatment, and said solvent containing the extracted phytochemical is continuously separated as a result of said centrifugal force.

Figure 4A:
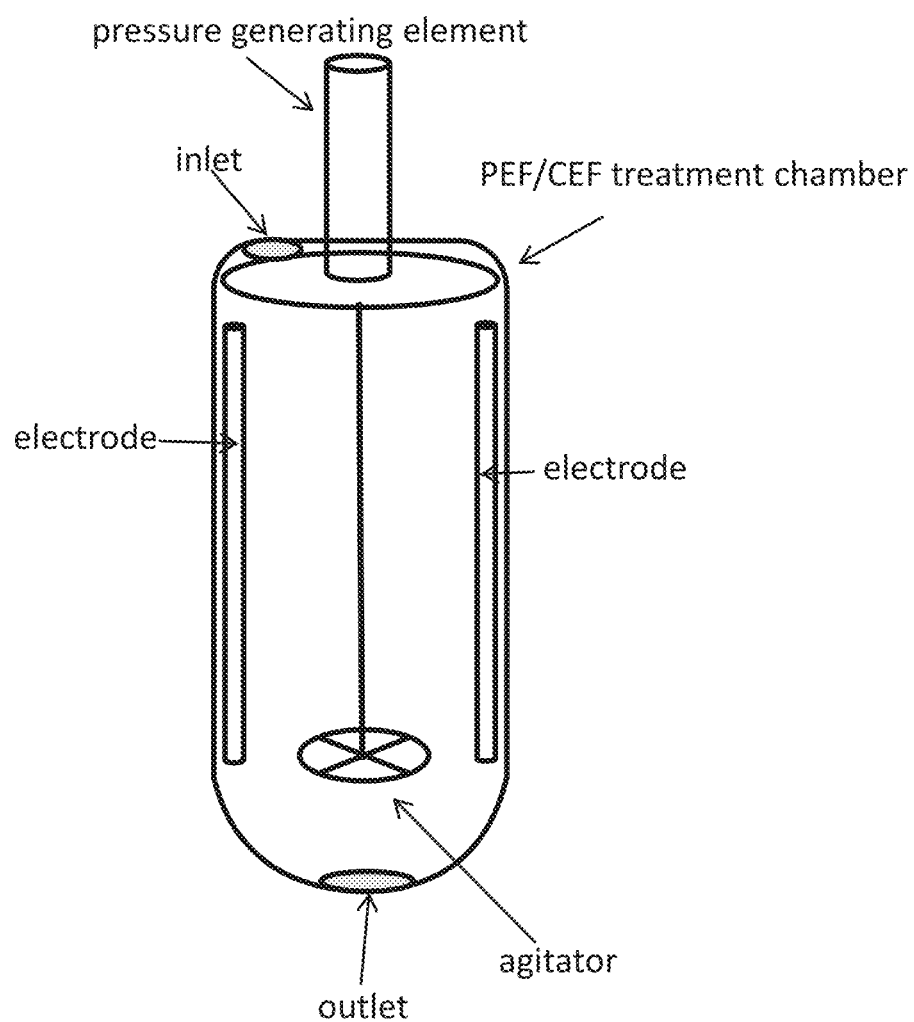
FIGS. 4A-4C schematically illustrate certain configurations of a device for the extraction of a phytochemical from a macroalgae, as disclosed herein.
Figure 4B:
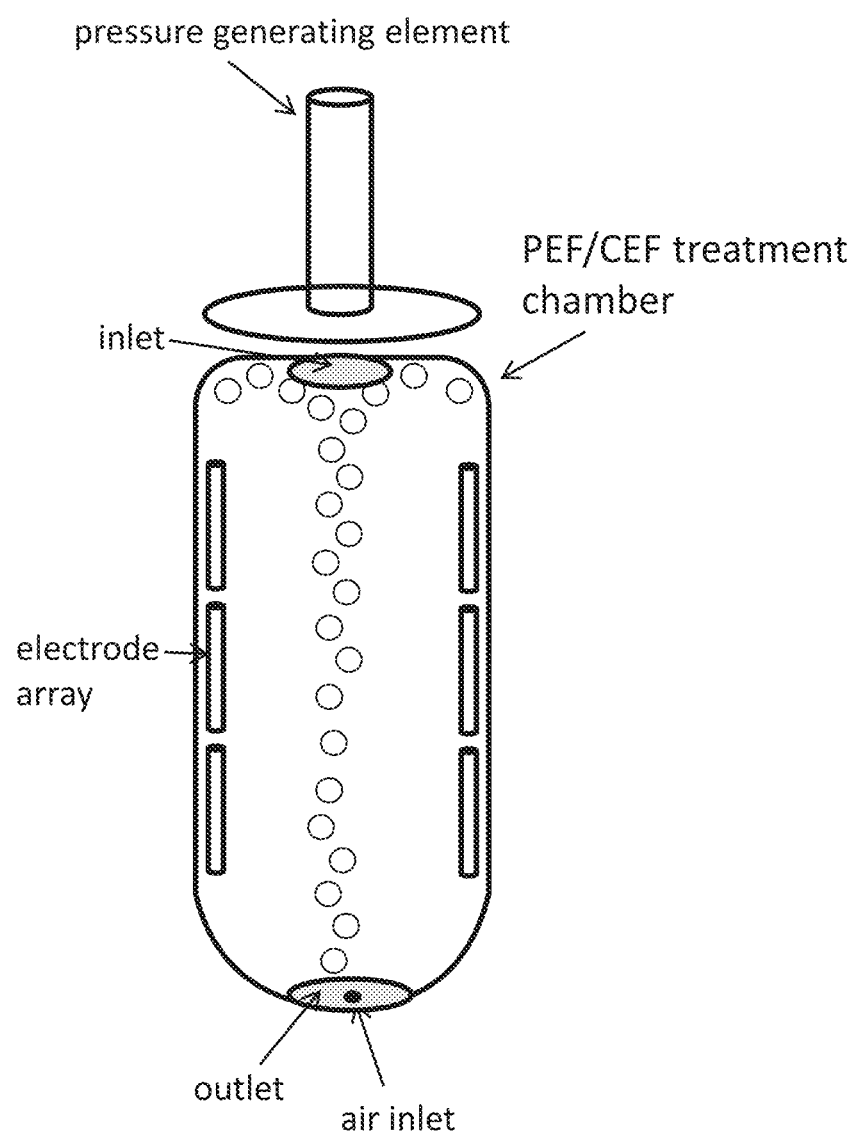
Figure 4C:
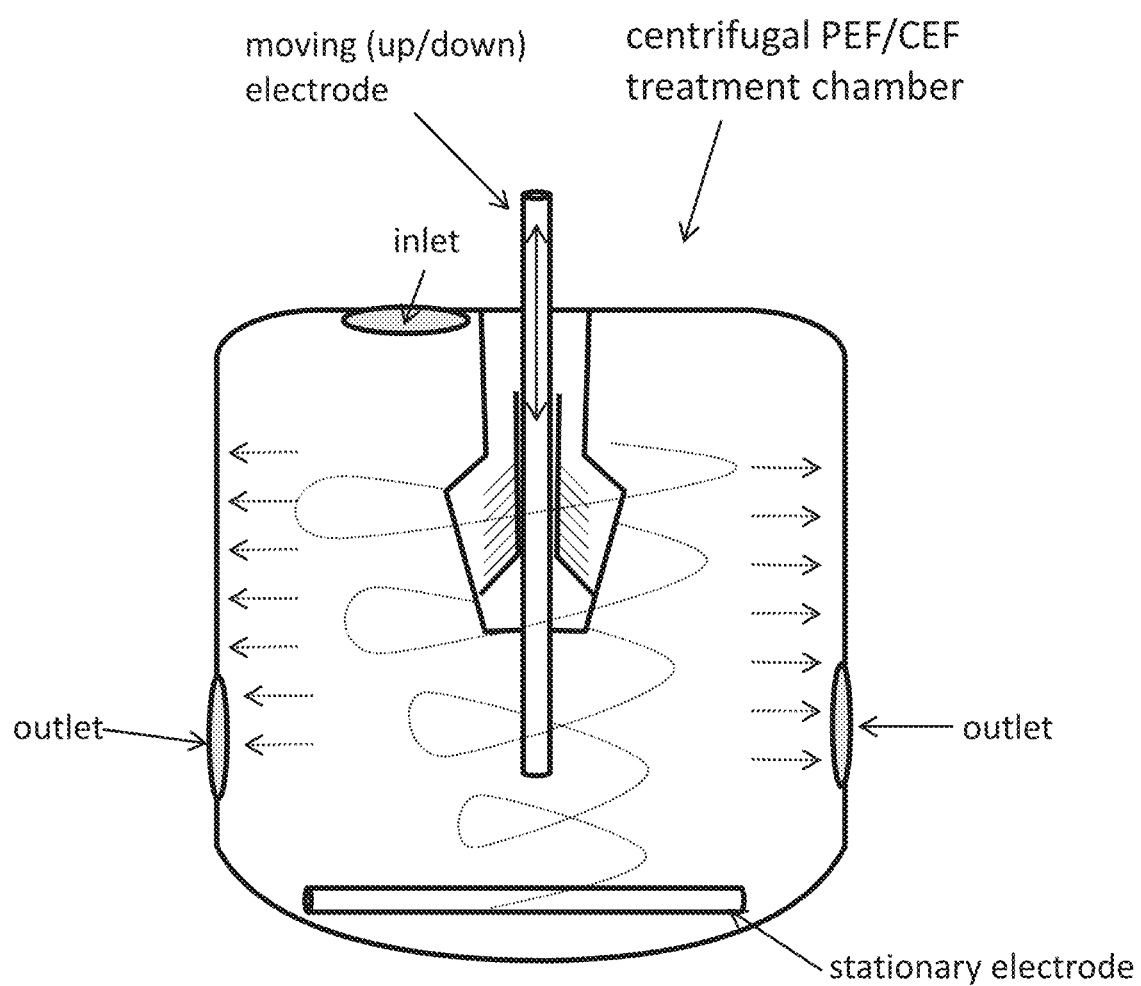

FIGS. 4A-4C schematically illustrate certain configurations of a device for the extraction of a phytochemical from a macroalgae, as disclosed herein. FIG. 4A depicts such a device comprising a PEF/CEF treatment chamber having an inlet located at its upper part, for inserting the solvent in which said macroalgae is submerged; an outlet located at its bottom, from which said solvent containing the extracted phytochemical exits upon completion of the PEF/CEF treatment; two electrodes located inside, and on opposite sides of, the chamber, for creating/generating the electric field needed for said PEF/CEF treatment; a mechanical pressure generating mean, e.g., a piston, for generating a pressure higher than the ambient pressure within/inside said chamber during said PEF/CEF treatment; and an agitator for stirring said solvent during said PEF/CEF treatment. FIG. 4B depicts another device comprising a PEF/CEF treatment chamber in which each opposing electrode is, in fact, an electrode array consisting of a plurality of electrodes each capable of generating the same or different electrical current. Such an electrode configuration enables creating different electric fields at different areas of the treatment chamber, which might be beneficial in certain cases, e.g., to reduce the total power consumed by the device. The treatment chamber shown in FIG. 4B lacks an agitator; however, comprises an air inlet through which air is poured into the chamber so as to stir the solvent during the PEF/CEF treatment. FIG. 4C depicts a further device comprising a PEF/CEF treatment chamber that is, in fact, a centrifuge (centrifugal chamber), wherein the PEF/CEF treatment is carried out under pressure higher than the ambient pressure resulting from the centrifugal force created by the rotation of said centrifuge during the PEF/CEF treatment, and solvent containing the extracted phytochemical is continuously separated as a result of said centrifugal force and exits the centrifuge via outlets. The electrode configuration illustrated in the device shown in FIG. 4C comprises a first moving (top-down) electrode, and a second stationary electrode located inside the treatment chamber.

Figure 5:
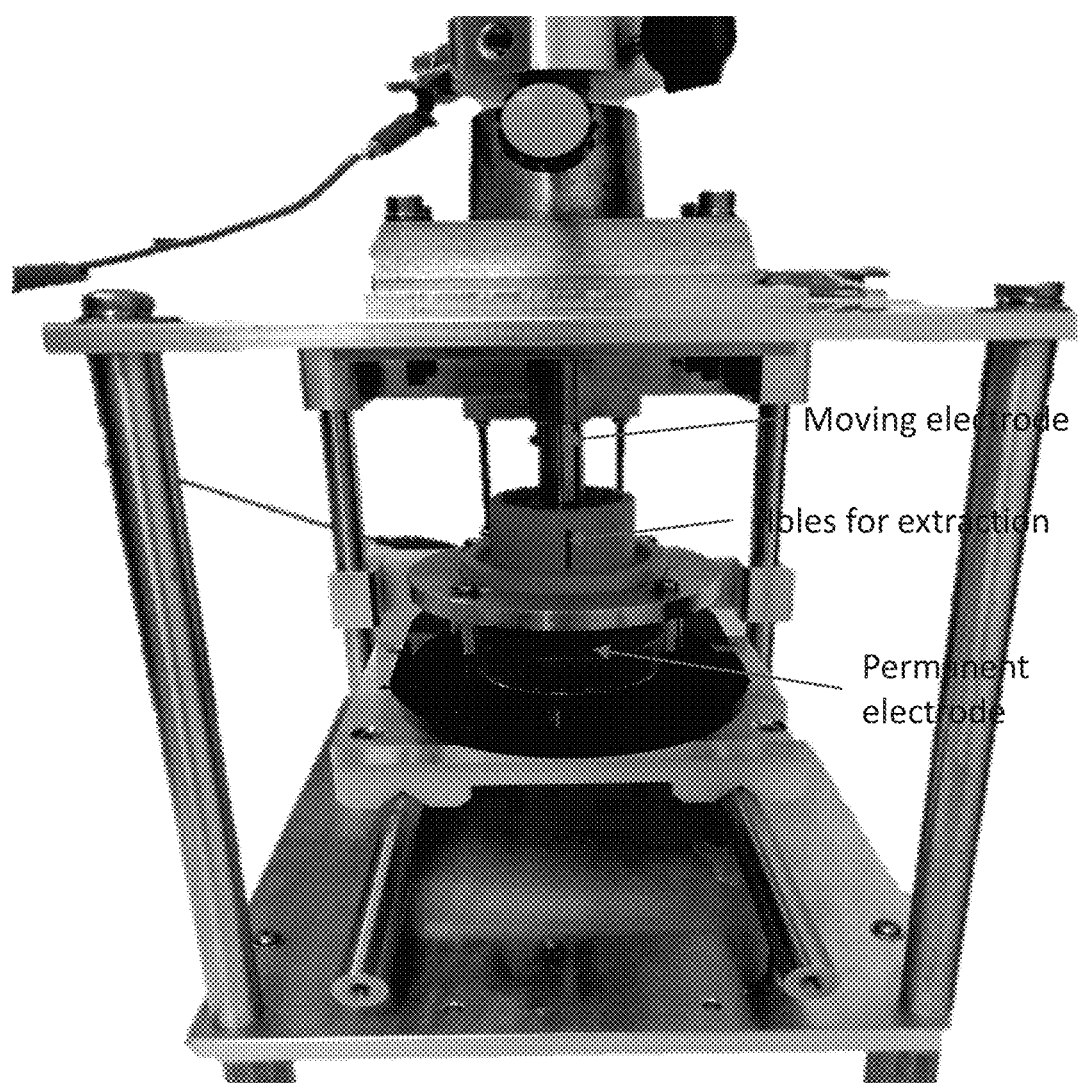
FIG. 5 shows a laboratory device for the extraction of a phytochemical from a macroalgae, as disclosed herein, based on the configuration illustrated in FIG. 4C, wherein the PEF/CEF treatment chamber is a centrifuge, and the outlets through which the solvent containing the extracted phytochemical continuously exits the chamber are positioned at the top of the chamber, thereby allowing the solvent containing the macroalgae to first undergo a PEF/CEF treatment under pressure higher than the ambient pressure, and only then move upward and exit the chamber.

FIG. 5 shows a laboratory device as disclosed herein, based on the configuration illustrated in FIG. 4C, wherein the PEF/CEF treatment chamber is a centrifuge. As shown, the outlets through which the solvent containing the extracted phytochemical continuously exits the treatment chamber are positioned at the top of the chamber, thereby allowing the solvent containing the macroalgae to first undergo a PEF/CEF treatment under pressure higher than the ambient pressure, and only then move upward and exit the chamber.

In still another aspect, the present invention provides a system for the extraction and separation of a phytochemical from a macroalgae, said system comprising: (i) a device as defined in any one of the embodiments above, for the extraction of said phytochemical from said macroalgae into said solvent; and (ii) a separation unit comprising at least one inlet and at least one outlet, for separating said phytochemical from said solvent, wherein upon extracting said phytochemical from said macroalgae into said solvent, said solvent is optionally filtered for removal of macroalgae debris; and said phytochemical is then separated from said solvent in said separation unit.

In certain embodiments, the treatment chamber and the separation unit constituting the system of the present invention are fluidly connected. In particular such embodiments, said treatment chamber and separation unit are fluidly connected via a one-way valve system.

In certain embodiments, the separation unit of said system comprises binding means having affinity to the phytochemical of interest, for reversibly binding said phytochemical. Such binding means may have functional groups capable of reversibly interacting with functional groups of said phytochemical. Such a separation unit may be, e.g., a chromatography, i.e., separation, column, into which the solvent containing inter alia said phytochemical, obtained from the extraction process carried out in the treatment chamber, is poured. While passing through the column, the phytochemical of interest is adsorbed to the stationary phase, and after washing the stationary phase, said phytochemical is eluted using an appropriate eluent. Alternatively, said binding means having affinity to the phytochemical of interest are in the form of beads. Such beads may be added to the solvent obtained from the extraction process before, during or after introducing into the separation unit, and then treated outside the separation unit so as to release the bound phytochemical; or may be adhered to the wall of said separation unit.

In certain embodiments, the treatment chamber and the separation unit of the system of the present invention constitute the same chamber.

In certain embodiments, the separation unit of said system is a centrifuge. The option for separating the phytochemical of interest using a centrifuge might be relevant, e.g., in cases wherein the molecular weight of said phytochemical is substantially different, e.g., substantially higher, than the molecular weights of the other components extracted from said macroalgae cells into the solvent during the CEF- or PEF-treatment.

In certain embodiments, the separation unit of said system is a filtration system, such as a tangential flow system where the solution obtained from the extraction process flows through a feed channel and along (tangent to) the surface of the membrane as well as through the membrane, as described in detail in, e.g., http://www.pall.com/main/laboratory/literature-library-details.page?id=34212.

Figure 6A:
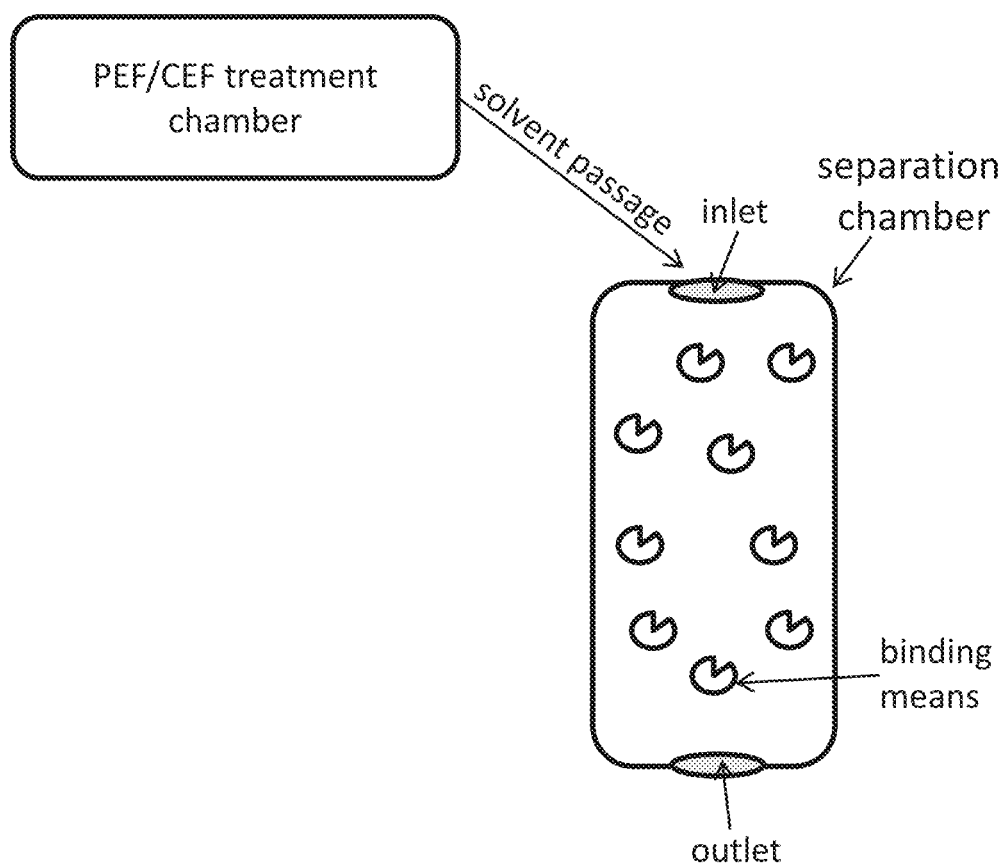
FIGS. 6A-6B schematically illustrate certain configurations of a system for the extraction and separation of a phytochemical from a macroalgae, as disclosed herein.
Figure 6B:
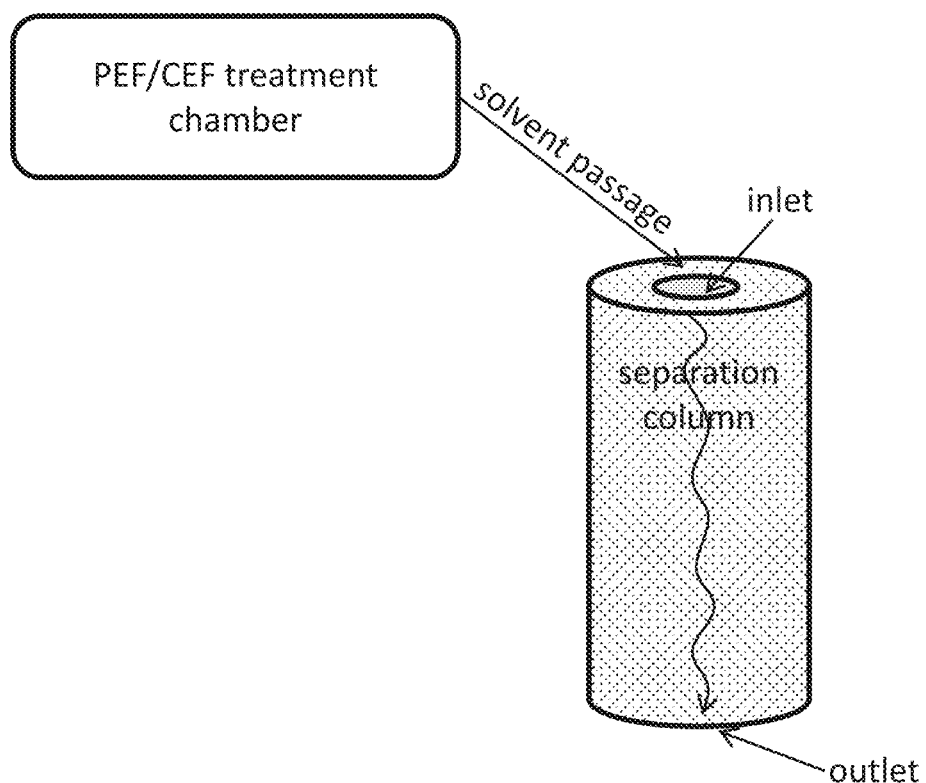

FIGS. 6A-6B schematically illustrate certain configurations of a system for the extraction and separation of a phytochemical from a macroalgae, as disclosed herein, comprising a device for the extraction of a phytochemical from a macroalgae, as defined in any one of the embodiments above including those schematically depicted in FIGS. 4A-4C, and a separation unit for separating the extracted phytochemical from said solvent. FIG. 6A depicts such a system, wherein the separation unit is a chamber comprising binding means having affinity to said phytochemical, more specifically wherein said binding means are in the form of beads. According to the present invention, such beads may be introduced into the separation chamber prior to the separation step (as shown in the figure), either before or after introducing the solvent containing the extracted phytochemical; or may be adhered to the wall of the separation chamber (not shown). FIG. 6B depicts a different configuration, wherein the separation unit is a chromatography- or separation-column. The various technologies that might be utilized for separating the extracted phytochemical of interest from the solvent, depending on the particular separation unit used, are well-known to any person skilled in the art.

Fossil resources have driven the economy throughout the world; however, the limits of fossil-based economies are now obvious. Indeed, environmental consequences, depletion of Earth's fossil resource and unbalanced geographical reparation have been of growing concern in the last three decades and most countries are now switching to alternative sources of energy. Among those alternatives, biomass is expected to play a key role in the transition from a fossil-based economy to sustainable ones. Numerous efforts are already deployed to build and support a biomass industry, notably through feedstock improvement, better supply chain, new applications, and products, or new processes. However, many challenges still remain in both upstream biomass processing, e.g., feedstock growth, transport or storage, and downstream biomass processing, e.g., pretreatment, pyrolysis, gasification, fermentation or extraction. Most downstream processing challenges arise from the fact that biomass constituents are difficult to fractionate. Therefore, the share of constituents of interest in any biomass feedstock for a particular process, e.g., sugar or polysaccharide for ethanol fermentation, is a crucial parameter on the overall efficiency of such process.

Removing non-target constituents, which would often become feedstock of another processing unit, improves the final yield of the target product and prevents those unnecessary substances to disturb the process. Ash content of biomass is a good example of such hurdle. The term "Ash" refers to the residue left after the combustion of a biomass sample at medium temperature (usually 400-600° C.) that removes organic matter (C, H, O and N). Today ash fraction has small value compared to other biomass constituents, such as sugar, protein, lipid, pigments, phenolic compounds, etc., and is also known to significantly affect various biomass-processing operations, notably thermal treatments such as pyrolysis, gasification, combustion, or hydrothermal treatment that are sensitive to ash content, which leads to equipment degradation and lower product quality. Moreover, ash can also disturb enzymatic treatment and fermentation.

To address these destructing effects of ash, various deashing pre-treatments such as washing biomass with water or various chemical solutions have been investigated or proposed. More advanced technologies utilizing an ion-exchange resin, ion-exchange membrane, or electrodialysis can be used to remove ash from the liquid stream; however, their direct applications on solid biomass have not been reported so far. Water washing uses a considerable amount of water (several liters per kg of biomass) and has a limited efficiency. On the other hand, washing with an acid or alkali solution has been shown to increase the removal of ash; however, usually requires a subsequent neutralization step that requires an additional amount of water and/or chemicals. Overall, considerable liquid waste streams are produced during the washing treatment and subsequent neutralization step, making chemical washing treatment difficult and environment-unfriendly. Moreover, handling of considerable volumes of strong acid and alkali solutions in industrial facilities is more expensive and requires specific installations and safety policies.

Although a considerable amount of ash can be found on the surface of the biomass, various biomass contains a high level of intracellular ashes that are even harder to remove by washing.

Study 2 herein shows that PEF treatment followed by hydraulic pressing was able to drastically increase the extraction yield of ash from fresh seaweed biomass leading to the extraction of 39.7±5.3% of the initial ash content compared to 18.4±1.1% for hydraulic pressing alone. PEF treatment could therefore be used as a quick, water efficient, energy efficient, scalable, continuous or discontinuous, mild thermal and non-chemical pretreatment for deashing biomass without significantly impacting its valuable constituents. The proposed pretreatment is particularly promising for ash removal, nutrient recovery and dewatering of biorefinery feedstock, notably of the marine source.

In a further aspect, the present invention thus relates to a method for deashing a cell biomass by applying PEF- or CEF-treatment, preferably non-thermal PEF or CEF treatment, more preferably non-thermal PEF treatment, to said cell biomass in a solvent, optionally under pressure higher than the ambient pressure, thereby extracting ash fraction from said cell biomass into said solvent. More particularly, the invention provides a method for improving a cell biomass, said method comprising deashing, i.e., extracting ash fraction from, said cell biomass by applying PEF- or CEF-treatment, preferably non-thermal PEF or CEF treatment, more preferably non-thermal PEF treatment, to said cell biomass in a solvent, optionally under pressure higher than the ambient pressure. In certain embodiments, this method is carried out under ambient pressure, i.e., without applying an external force/pressure. In other embodiments, the method is carried out under pressure higher than the ambient pressure, e.g., by applying an external force/pressure such as a mechanical or centrifugal force.

The term "cell biomass" as used herein means a biomass comprising a plant, e.g., an aquatic plant, or an animal tissue, bacterial cells, fungal cells, of a biofilm. In certain embodiments, the cell biomass treated thus improved by the method of the invention is a plant tissue biomass, e.g., an aquatic plant tissue biomass (seaweed) such as macroalgae biomass. In other embodiments, the cell biomass treated is an animal tissue. In further embodiments, the cell biomass treated comprises bacterial or fungal cells, or biofilm, e.g., bacterial biofilm. Biomass treated according to this method, e.g., plant- or seaweed-biomass, may then be used as an improved feedstock.

The ash fraction extracted from the cell biomass by the method of the invention comprises inorganic material, e.g., a chemical element such as phosphorus or a metal. In still a further aspect, the present invention thus relates to a method for extraction of a chemical element from a cell biomass, e.g., a plant biomass such as seaweed biomass, said method comprising applying PEF- or CEF-treatment, preferably non-thermal PEF or CEF treatment, more preferably non-thermal PEF treatment, to said cell biomass in a solvent, optionally under pressure higher than the ambient pressure, thereby extracting said chemical element from said cell biomass into said solvent. In certain embodiments, this method is carried out under ambient pressure, i.e., without applying an external force. In other embodiments, the method is carried out under pressure higher than the ambient pressure, e.g., by applying an external force such as a mechanical or centrifugal force. In some embodiments, the chemical element extracted by this method is phosphorus (P). In other embodiments, said chemical element is a metal, e.g., a valuable metal, a transition metal, or a heavy metal, such as lithium (Li), titanium (Ti), rhodium (Rh), silver (Ag), rhenium (Re), platinum (Pt), gold (Au), thorium (Th), and uranium (U). The method disclosed herein may further comprise a step of separating said chemical element from said solvent.

The various parameters characterizing the methods disclosed hereinabove, i.e., the those characterizing the PEF treatment by pulse number, pulse duration, electric field strength, and pulse frequency; and those characterizing other aspect of the process such as the solvent used, the temperature being developed in the solvent during said PEF- or CEF-treatment, and the external pressure if applied during the PEF/CEF treatment, can be selected from any of the options defined in any one of the embodiments above.

Unless otherwise indicated, all numbers expressing, e.g., PEF characteristics such as pulse number, pulse duration, electric field strength, and pulse frequency, pressure applied during the PEF/CEF treatment, or temperature developed in the solvent subjected to the PEF/CEF treatment during said treatment, used in the specification are to be understood as being modified in all instances by the term "about". Accordingly, unless indicated to the contrary, the numerical parameters set forth in this specification are approximations that may vary by up to plus or minus 10% depending upon the desired properties sought to be obtained by the present invention.

The invention will now be illustrated by the following non-limiting Examples.

EXAMPLES

Study 1. Extraction of Proteins Extraction from Macroalgae *Ulva* with PEF

Materials and Methods

Biomass Material.

*Ulva* biomass was obtained from Alga Plus Company, Portugal (cultivated in the certified integrated aqyaculture facility). Macroalgae were then stored for 2 days in a 400 L aquarium with a salt concentration of 3.5%.

PEF Treatment.

The fresh biomass was centrifuged at about 840 rpm for 3 runs of 1 min each to remove the external water, so that <5 g of water have been removed during the third run. 140 g of *Ulva* biomass in a 2 L becher was weighted with scale of type KERN 440-49N. This amount of macroalgae was then poured and pushed into the PEF treatment chamber with a volume of 232 $cm^3$ for the application of a homogeneously distributed PEF. Water was added to the macroalgae to fill the chamber completely. The chamber was closed to begin the PEF treatment. After the PEF treatment was applied, the macroalgae were collected and returned to the becher. The electroporated macroalgae were weighted again. The treatment parameters were: average field strength (average was taken between all pulses at all repeats, 225 measurements) 2.964±0.007 kV cm$^{-1}$, and pulse duration 5.70±0.30 µs, delivered at 0.5 Hz. These parameters were chosen based on the previous studies with PEF dehydration of various types of biomass with this system (Sack et al., 2009; Sack et al., 2010a; Sack et al., 2010b; Sack et al., 2008). Temperature was measured with a digital thermometer (TFA Type 30.1018). Current and voltage across the electrodes of the treatment chamber during each pulse were measured with a current probe (PEARSON 110 A) and a voltage divider (HILO-Test HVT 240 RCR), both connected to an oscilloscope (Tektronix TDS 640A). The impedance of the treated sample was derived from the current and voltage measurements.

Energy Consumption.

The total energy consumed for the PEF treatment was calculated based on the energy stored in the pulse capacitor with the following Eq. 1:

$$E_t = 0.5 * C * 10^{-9} * (V * 10^3)^2 * N \quad \text{Eq. 1}$$

where Et (J) is the total energy consumed for the treatment of one treatment chamber, C is the discharging capacitor capacitance (nF), V (kV) is the applied voltage and N is the total number of pulses. Additional losses of the capacitor charger have not been considered.

The energy consumed with PEF for protein extraction was than calculated with Eq. 2:

$$E_p = \frac{E_t}{m} \Big/ (C_p * m_{PEF}) \quad \text{Eq. 2}$$

where Ep (kWh kg$^{-1}$) is the PEF energy required to extract 1 g of protein, Et (kWh kg$^{-1}$) is the total energy consumed to treat the PEF chamber, m (kg) is the raw mass of treated macroalgae, $C_p$ (kg mL$^{-1}$) is the concentration of the proteins in the extracted juice, and mPEF (mL) is the volume of the extracted juice.

Mechanical Juice Extraction.

The electroporated algae were placed in a cloth material that was folded so that the algae could not escape during pressing. The algae wrapped up in the fabric were placed in the mechanical press (HAPA type SPM 2.5S). A force of 45 daN cm$^{-2}$ was applied for a determined time of 5 min using the automatic mode of the press that keeps the pressure applied to the piston constant. Extracted juice from pressing was collected in a 2 L becher and weighted at the end of the pressing. The pressed material was taken out of the press, weighted, reorganized and put back into the press for a second pressing step. The extracted juice and the pressed algae were again weighted.

Crude Protein Quantification.

Bovine serum albumin (BSA) in DDW calibration curve was done in following concentrations: 1 mg/mL, 500 µg/mL, 250 µg/mL, 200 µg/mL, 150 µg/mL, 100 µg/mL, 50 µg/mL, 25 µg/mL and 0 µg/mL. Every 10 µL BSA concentration mixed with 115 µL Bradford buffer. Extracted juice was filtered with 0.2 µm filter, 10 µL of samples mixed with 115 µL Bradford buffer. The BSA concentrations and the extracted juice samples with Bradford buffer measured in optical density (OD) 450 nm and 590 nm. The numbers of OD 450 parts 590, were the basis for linear calibration curve. OD detection was done with an EL808, BioTek spectrophotometer (Winooski, Vt., USA).

Gel Electrophoresis.

Extracted juice from pressing with/without PEF treatment was filtered with a 0.2 µm filter. Protein precipitation was made: 1 volume of trichloroacetic acid (TCA) 100% (w/v) added to 4 volumes extracted juice samples. Then moved to 1.5 mL tubes. The samples incubated in 10 min at 4° C. The tube spin in microcentrifuge at 14K rpm, 5 min. Supernatant was removed, protein left in the pellet intact. Pellet was washed with 200 µl cold acetone. Spin in microfuge at 14 K rpm, 5 min. We made total of 2 acetone washes. Pellet was dried by placing tube in 95° C. heat block for 5-10 min. SDS-PAGE, 4× sample buffer (with βME) and sample boiled for 10 min in 95° C. heat block. The samples were loaded onto polyacrylamide Gel. Samples run on SDS gel 12% agarose 200 V, 30 min.

Extracted Proteins Identification Quantification with LS-MS/MS.

Proteolysis.

200 µL of the samples was brought to 8 M Urea. The protein in 8 M Urea was reduced with 2.8 mM DTT (60° C. for 30 min), modified with 8.8 mM iodoacetamide in 100 mM ammonium bicarbonate (in the dark, room temperature for 30 min) and digested in 2 M Urea, 25 mM ammonium bicabonate with modified trypsin (Promega) at a 1:50 enzyme-to-substrate ratio, overnight at 37° C. One microgram from each sample was injected into a LC-MS/MS device.

Mass Spectrometry Analysis.

The tryptic peptides were desalted using C18 tips (Homemade stage tips) dried and re-suspended in 0.1% formic acid. The peptides were resolved by reverse-phase chromatography on 0.075×180-mm fused silica capillaries (J&W) packed with Reprosil reversed phase material (Dr Maisch GmbH, Germany). The peptides were eluted with linear 60 min gradient of 5-28% 15 min gradient of 28-95% and 15 min at 95% acetonitrile with 0.1% formic acid in water at flow rates of 0.15 µl/min. Mass spectrometry was performed by a Q Exactive plus mass spectrometer (Thermo) in a positive mode using repetitively full MS scan followed by collision induces dissociation (HCD) of the 10 most dominant ions selected from the first MS scan.

Computational Analysis.

The mass spectrometry data was analyzed using either the MaxQuant software 1.5.1.2 (Mathias Mann's group) or Peaks 7 software (Bioinformatic Solutions). The analyses were done vs. the green algea section of the NCBI-nr database with 1% false discovery rate (FDR). The data was quantified by label free analysis using the same software. Intensity parameter mean: Summed up eXtracted Ion Current (XIC) of all isotopic clusters associated with the identified AA sequence. For specific protein quantification, the intensity measured for each protein was normalized to the total intensity of all proteins from the same sample.

Statistical Analysis.

Statistical analysis was performed with Excel (ver. 13, Microsoft, WA) Data analysis package. All experiments and controls were done in triplicates unless stayed differently. Standard error of the mean (SEM) is shown in error bars. One side Student's t-test was performed for compare the total protein extraction yield to controls. MS statistical analysis for proteins identification was done as described in Computational analysis. The criterion for inclusion was that the same protein was identified in at least two repeats from three.

Results

Process of Proteins Extraction from Macroalgae Ulva with PEF

First, we analyzed the shape of the individually delivered electric pulse. Because of the cell membrane electroporation, the resistance of the treated macroalgae biomass reduces. Therefore, we expected mild changes in the shape and pick values of each individual pulse. FIG. 1 shows the shape of delivered voltage and current at the first (U1, I1) and last (U_last, I_last) pulse in the delivered series of 75 pulses. The pulse source has been designed such, that a series of pulses of equal energy are applied. A pulse circuit based on a capacitor discharge has been employed. For a series of pulses the charging voltage of the capacitor has been kept constant. Pulses with an aperiodically damped shape are applied to the load. The peak current of the pulse is influenced by the resistance of the electrode system inside the treatment chamber and the stray inductance of the pulse circuit. The resistance of the treatment chamber decreases with the number of applied pulses, as discussed later. As a consequence, the pulse shape changes with the decreasing resistance, and the voltage across the electrode system decreases slightly with increasing number of pulses.

PEF Parameters and Changes in the Macroalgae Biomass During Extraction

Figure 2:
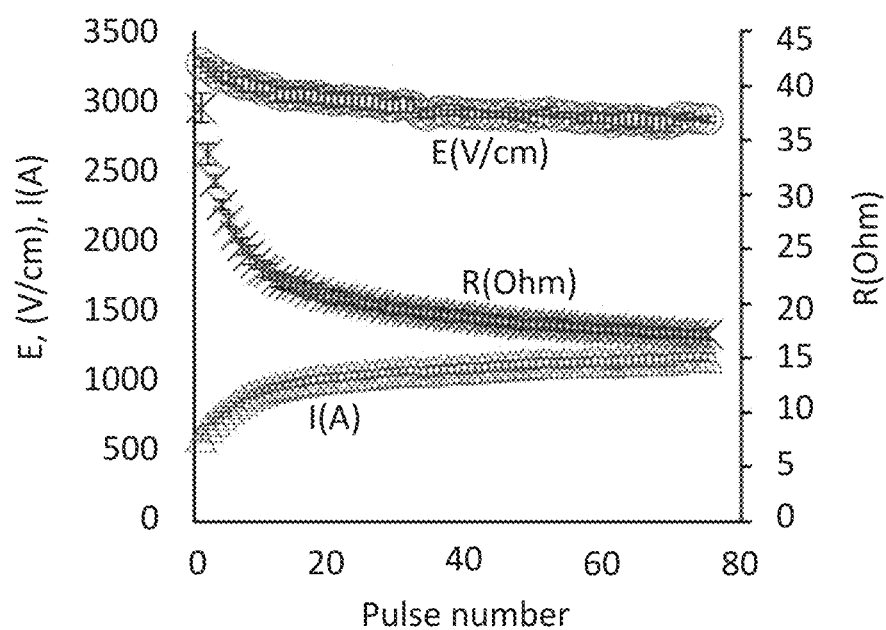
FIG. 2 shows PEF and sample resistance behavior during macroalgae biomass treatment. Critical process parameters such as electric field (E), current (A) and biomass resistance (R) were monitored during each pulse. The experiment was done in triplicate. Error bars show ±SEM.

Next, we analyzed the changes in the peak electric field and current during the whole treatment (FIG. 2). We observed the decrease of the actual delivered electric field strength per pulse and increase of the current per pulse. These changes are expected because of treated media conductivity increase (FIG. 2 shows the decrease in the resistance), which follows cell membrane electroporation and release of intracellular cell content. In the application of 75 pulses on the biomass, the actual peak electric field decreased from $3.215\pm0.033$ kV cm$^{-1}$ at the beginning of the treatment (first five pulses) to $2.864\pm0.040$ kV cm$^{-1}$ at the end of the treatment (last five pulses in the series). The current increased from $713.6\pm16.8$ A at the beginning of the pulse series (first five pulses) to $1173.86\pm30.8$ A. These changes in the actual electric field and current are explained by the 46% drop of the sample resistance during the application of PEFs. Interesting, we observed that the major decrease in the resistance (35%) and increase in the current from $713.6\pm16.8$ A to $1024\pm26.7$ A took place during the first twenty pulses. This is probably the number of pulse required to electroporation the majority of cells in the treated Ulva thalli. Previously, we have observed similar pattern of rapid resistance decrease and current increase in the skin tissue, where electric fields also electroporated cells inside the complex extracellular matrix (Golberg et al., 2013) and also in sugar beet tissue (Bluhm and Sack, 2008).

Extracted Proteins Yield

Figure 3:
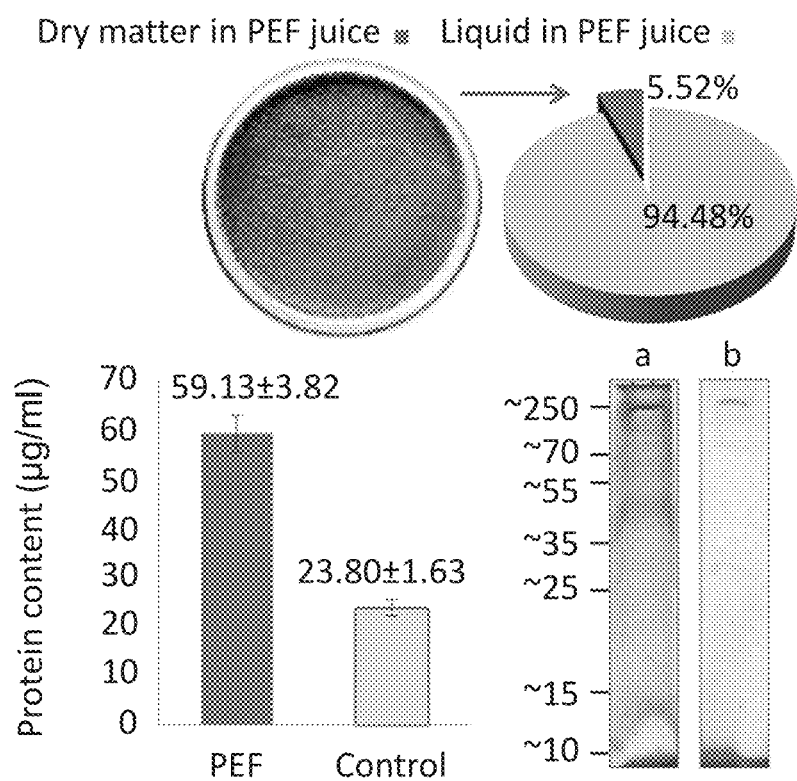
FIG. 3 shows proteins extraction from *Ulva*. SDS gel electrophoreses (right) and total protein quantification with Bradford (left) process parameters and total yields for 24 kV, 75 pulses applied. Error bars show ±SEM. Insert in the top row shows the total water-soluble solids extracted from *Ulva* with PEF.

With the treatment parameters used in this study the average electric field strength applied on the macroalgae thalli was $2.964\pm0.007$ kV cm$^{-1}$, the pulse duration was $5.70\pm0.30$ μs. The total dry matter consisted $5.52\pm0.20$% of the total extracted juice weight (FIG. 3). PEF increased the total protein extraction yields ($p<10^{-6}$). The total protein concentration in the extracted juice was $59.13\pm3.82$ μg μL$^{-1}$, which is in contrast to $23.80\pm1.33$ μg μL$^{-1}$ observed in the control samples (FIG. 3). Importantly, the developed process has almost no thermal effects on the produced proteins as the maximum observed temperature was $35.50\pm2.02°$ C.

PEF Process Energy Consumption

An important parameter in the production of proteins for food and feed applications is the energy consumptions. Non-thermal PEF has been shown previously to reduce the total energy consumption of the sugar extraction by 30-50% at the industrial scale (Bluhm and Sack, 2008; Sack et al., 2010a; Sack et al., 2010b). Here we analyzed the energetic consumption of the PEF process for water soluble solids, including proteins, extraction from macroalgae Ulva. The specific energy consumed relative to raw mass of macroalgae was $8.56\pm0.01$ Wh kg$^{-1}$ ($30.81\pm0.03$ Li kg$^{-1}$) and the specific energy relative to the extracted proteins was $251\pm3$ kWh kg$^{-1}$.

PEF Extracted Proteins Identification

Previous works has shown the use of PEF to extract proteins from microalgae (Goettel et al., 2013; Parniakov et al., 2015), yeast (Ganeva and Galutzov, 1999; Ganeva et al., 2003), bacteria (Haberl Meglic et al., 2015) and plants (Bluhm and Sack, 2008; Doevenspeck, 1961; Sack and Bluhm, 2008; Vorobiev and Lebovka, 2010; Zagorulko, 1958). However, to the best of our knowledge these were reported as crude protein extraction. In this work we identified and quantified specific proteins extracted from Ulva genus with PEF using LC/MS/MS (Table 1 shows all identified proteins in at least one sample). Proteins that have been uniquely identified in the PEF treated samples extracts appear in Table 2 (showing proteins that have been identified in at least two repeats from three). Proteins detected only in samples from Ulva biomass treated only with water, appear in Table 3 (showing proteins that have been identified in both of the two repeats). These proteins were not observed in the PEF treated samples and probably have been damaged by electric fields. Table 4 lists the proteins that have been detected in both PEF treated and non-treated samples. Interesting, we observed that besides Plastocyanin precursor, PEF reduced the quantities of proteins extracted from Ulva biomass with the tap water (based on intensity parameter). Our previous work with DNA showed that specific PEF parameters lead to DNA nicking (Golberg and Rubinsky, 2010). Additional studies showed that specific PEF parameters could lead to either activation or inactivation of enzymes, depending on enzyme type (Ohshima et al., 2007). However, most of the studies until today showed that PEF increases the extraction yields. Indeed, in our study PEF increased about 3 times the extracted proteins yield if measured in a bulk. However, the detailed identification and quantification of individual proteins, reported here for the first time, reveals a more complex scenario. Some proteins are extracted with PEF (Table 2 and Table 4), but some, which can be extracted with the tap water are partially (Table 4) or completely (Table 3) degraded by the treatment. To the best of our knowledge this is a first report that identified proteins extracted from biomass with PEF; previous studies used bulk proteins characterization (Coustets et al., 2015; Ganeva et al., 2003). These finding are new and important, as they open a possibility to optimize PEF parameters for the extraction of specific proteins from macroalgae and other biomass. An important future application could be the inactivation of the ingenious proteases during protein extraction processes. Additional future studies will address the effect of PEF extraction on the functional properties of the extracted proteins. PEF provides a potentially unique non-thermal, chemicals-free proteins extraction method that could preserve the functional properties of the proteins, important for food and pharmaceutical applications.

Conclusions

Macroalgae are promising, but challenging sustainable feedstock for biorefineries. Complete zero waste conversion of macroalgae into food, chemicals and fuels will reduce the burden of the agriculture from arable land. The present study provides a new technology for the extraction of green macroalgae Ulva proteins with electroporation by PEF, which is an emerging, energy efficient technology for biomass processing. The present study shows that PEF increases by about three times the total protein extraction, and is selective, as it increases the extraction yields of some specific proteins but damages others. This study demonstrates the scalable, energy efficient technology for extraction essential for food supply chemicals-proteins, from macroalgae.

TABLE 1

Proteins identified in at least one sample (+/−PEF treated samples/controls)

| Protein identification | NCBI accession number (GI) | Protein found in the species | MW (kDa) | Average intensity (−PEF) | Average intensity (+PEF) |
|---|---|---|---|---|---|
| Actin | 116222105 | *Pterosperma cristatum* | 38 | 4.79E+07 | 3.10E+06 |
| Actin | 821690933 | *Chlamydomonas moewusii* | 41 | 3.03E+07 | — |
| Actin | 303283626 | *Micromonas pusilla* CCMP1545 | 41 | 7.06E+06 | 3.45E+06 |
| Actin | 612392888 | *Bathycoccus prasinos* | 41 | 5.28E+07 | — |
| Alpha tubulin | 255088289 | *Micromonas* sp. RCC299 | 49 | 2.50E+07 | 4.63E+06 |
| Amidohydrolase 2 | 693500897 | *Ostreococcus tauri* | 35 | 2.14E+08 | — |
| Calmodulin | 654126732 | *Tetraselmis* sp. GSL018 | 16 | 2.66E+07 | — |
| Calreticulin | 255089467 | *Micromonas* sp. RCC299 | 48 | — | 2.57E+07 |
| Cytosolic 80S ribosome and 40S small subunit | 302839477 | *Volvox carteri f. nagariensis* | 16 | 3.45E+07 | — |
| Disulfide isomerase 1 | 222431913 | *Ulva fasciata* | 60 | — | 5.92E+06 |
| Elongation factor 1-alpha | 148524153 | *Acetabularia acetabulum* | 47 | 1.71E+07 | 1.14E+07 |
| Ferredoxin-NADP$^+$ reductase | 545356935 | *Coccomyxa subellipsoidea* C-169 | 38 | — | 6.26E+07 |
| Fructose-1,6-bisphosphatase | 145345160 | *Ostreococcus lucimarinus* | 35 | — | 3.53E+07 |
| Fructose-bisphosphate aldolase 1 | 302831241 | *Volvox carteri f. nagariensis* | 41 | — | 3.42E+07 |
| Heat shock protein 70 | 304555563 | *Ulva pertusa* | 73 | 2.80E+07 | 4.81E+06 |
| Histone H3 (partial) | 159465881 | *Chlamydomonas reinhardtii* | 9 | — | 6.61E+06 |
| Histone H4 | 761973387 | *Monoraphidium neglectum* | 11 | 1.33E+07 | — |
| Histone H4 (partial) | 157043072 | *Dunaliella sauna* | 10 | — | 2.13E+07 |
| Iron-superoxide dismutase 1 | 149275667 | *Ulva fasciata* | 25 | 3.04E+07 | 9.46E+06 |
| Iron-superoxide dismutase 2 | 149275669 | *Ulva fasciata* | 22 | 1.04E+08 | 5.39E+06 |
| Lactate dehydrogenase/ glycoside hydrolase | 633909566 | *Helicosporidium* sp. ATCC 50920 | 14 | 8.54E+06 | 9.24E+06 |
| Phosphoglycerate kinase | 654120603 | *Tetraselmis* sp. GSL018 | 45 | — | 2.30E+07 |
| Photosystem I iron-sulfur center, partial (plastid | 269925003 | *Volvox carteri f. nagariensis* | 3 | 2.56E+07 | — |
| Plastocyanin | 3024399 | *Ulva pertusa* | 11 | 1.59E+09 | 1.27E+09 |
| Plastocyanin precursor | 48526878 | *Ulva pertusa* | 15 | 8.24E+08 | 2.14E+09 |
| Ran G-protein (partial) | 19852117 | *Acetabularia acetabulum* | 6 | 1.71E+07 | — |
| Ribosomal protein L12 (chloroplast) | 11467764 | *Nephroselmis olivacea* | 18 | 4.70E+07 | 11467764 |
| ribulose-1,5-bisphosphate carboxylase/oxygenase large subunit | 41016415 | *Ulva tanneri* | 20 | 1.86E+07 | 1.02E+07 |
| sedoheptulose-1,7-bisphosphatase | 545353814 | *Coccomyxa subellipsoidea* C-169 | 37 | 1.19E+07 | 1.02E+07 |
| sedoheptulose-1,7-bisphosphatase | 7544134 | *Chlamydomonas* sp. W80 | 40 | 2.93E+07 | 5.29E+06 |
| translation elongation factor Tu (partial) | 307931162 | *Pterospenna cristatum* | 39 | 8.11E+06 | 1.35E+07 |
| Ubiquilin | 654115610 | *Tetraselmis* sp. GSL018 | 56 | — | 3.59E+07 |
| Ubiquitin (partial) | 552821086 | *Chlorella variabilis* | 8 | 2.99E+07 | 3.00E+07 |
| Uroporphyrin-III C-methyltransferase | 303285200 | *Micromonas pusilla* CCMP1545 | 32 | 1.66E+08 | 1.01E+07 |
| Hypothetical protein | 612393855 | *Bathycoccus prasinos* | 36 | 3.28E+07 | — |
| Hypothetical protein | 761971964 | *Monoraphidium neglectum* | 113 | 1.82E+08 | 1.03E+07 |

TABLE 1-continued

Proteins identified in at least one sample (+/−PEF treated samples/controls)

| Protein identification | NCBI accession number (GI) | Protein found in the species | MW (kDa) | Average intensity (−PEF) | Average intensity (+PEF) |
|---|---|---|---|---|---|
| Hypothetical protein-Membrane-associated Apoptosis protein | 545366761 | Coccomyxa subellipsoidea | 121 | 4.17E+07 | — |
| Predicted protein | 303280339 | Micromonas pusilla CCMP1545 | 40 | 1.97E+07 | — |
| Predicted protein | 255082750 | Micromonas sp. RCC299 | 215 | — | 2.01E+07 |
| Predicted protein | 145346523 | Ostreococcus | 32 | — | 3.41E+07 |
| Predicted protein | 145348138 | Ostreococcus lucimarinus CCE9901 | 39 | 2.10E+09 | 3.78E+08 |
| Predicted protein | 158274897 | Chlamydomonas reinhardtii | 58 | 1.33E+07 | — |
| Predicted protein | 612389598 | Bathycoccus prasinos | 78 | — | 4.32E+06 |

TABLE 2

Proteins detected only after PEF treatment

| Protein identification | NCBI accession number (GI) | Protein found in the species | MW (kDa) | Average normalized intensity (N = 3) |
|---|---|---|---|---|
| Calreticulin | 255089467 | Micromonas sp. RCC299 | 48 | 2.57E+07 |
| Ferredoxin-NADP+ reductase | 545356935 | Coccomyxa subellipsoidea C-169 | 38 | 6.26E+07 |
| Fructose-1,6-bisphosphatase | 145345160 | Ostreococcus lucimarinus | 35 | 3.53E+07 |
| Fructose-bisphosphate aldolase 1 | 302831241 | Volvox carteri f. nagariensis | 41 | 3.42E+07 |
| Phosphoglycerate kinase | 654120603 | Tetraselmis sp. GSL018 | 45 | 2.30E+07 |
| Ribosomal protein L12 (chloroplast) | 11467764 | Nephroselmis olivacea | 18 | 4.70E+07 |
| Predicted protein | 145346523 | Ostreococcus | 32 | 3.41E+07 |
| Predicted protein | 612389598 | Bathycoccus prasinos | 78 | 4.32E+06 |

TABLE 3

Proteins detected with water without PEF treatment

| Protein identification | NCBI accession number (GI) | Protein found in the species | MW (kDa) | Average normalized intensity (N = 2) |
|---|---|---|---|---|
| Amidohydrolase 2 | 693500897 | Ostreococcus tauri | 40 | 2.14E+08 |
| Calmodulin | 654126732 | Tetraselmis sp. GSL018 | 16 | 2.66E+07 |
| Cytosolic 80S ribosome and 40S small subunit | 302839477 | Volvox carteri f. nagariensis | 16 | 3.45E+07 |
| Histone H4 | 761973387 | Monoraphidium neglectum | 11 | 1.33E+07 |
| Photosystem I iron-sulfur center, partial (plastid | 269925003 | Volvox carteri f. nagariensis | 3 | 2.56E+07 |
| Hypothetical protein | 612393855 | Bathycoccus prasinos | 36 | 3.28E+07 |
| Predicted protein | 158274897 | Chlamydomonas reinhardtii | 58 | 1.33E+07 |
| Predicted protein | 303280339 | Micromonas pusilla CCMP1545 | 40 | 1.97E+07 |

TABLE 4

Proteins detected in samples with PEF and without PEF treatment

| Protein identification | NCBI accession number (GI) | Protein found in the species | MW (kDa) | Average normalized intensity | |
|---|---|---|---|---|---|
| | | | | −PEF (N = 2) | +PEF (N = 3) |
| Actin | 116222105 | *Pterosperma cristatum* | 38 | 8.96E+07 | 3.40E+07 |
| Heat shock protein 70 | 304555563 | *Ulva pertusa* | 73 | 2.80E+07 | 4.81E+06 |
| Iron-superoxide dismutase 1 | 149275667 | *Ulva fasciata* | 25 | 3.04E+07 | 9.46E+06 |
| Plastocyanin | 3024399 | *Ulva pertusa* | 11 | 1.59E+09 | 1.27E+09 |
| Plastocyanin precursor | 48526878 | *Ulva pertusa* | 15 | 8.24E+08 | 2.14E+09 |
| Sedoheptulose-1,7-bisphosphatase | 545353814 | *Coccomyxa subellipsoidea* C-169 | 37 | 1.19E+07 | 1.02E+07 |
| Ubiquitin | 552821086 | *Chlorella variabilis* | 8 | 3.82E+07 | 2.57E+07 |
| Uroporphyrin-III C-methyltransferase | 303285200 | *Micromonas pusilla* CCMP1545 | 32 | 1.66E+08 | 1.01E+07 |
| Hypothetical protein | 761971964 | *Monoraphidium neglectum* | 113 | 1.82E+08 | 1.03E+07 |
| Predicted protein | 145348138 | *Ostreococcus lucimarinus* CCE9901 | 39 | 2.10E+09 | 3.78E+08 |

Study 2. Deashing Macroalgae Biomass by PEF Treatment

Materials and Methods

Algal Biomass.

The biomass source used in this study corresponded to the green macroalgal species of the *Ulva*, recently identified as *U. rigida* (Krupnik, in press), a seaweed of worldwide distribution and found in the intertidal and shallow waters within the Israeli Mediterranean Sea shores. Algae were taken from an outdoor seaweed collection at Israel Oceanographic & Limnological Research, Haifa (IOLR), Israel. The seaweeds were cultivated in 600 L tanks supplied with running seawater, aeration and weekly additions of 1 mM $NH_4Cl$ and 0.1 mM $NaH_2PO_4$ (Friedlander, 2008).

With each nutrient addition, the water exchange was stopped for 24 h to allow for their absorption. About 3.0 kg of fresh *U. rigida* were packed in a sealed plastic bag and delivered to Karlsruhe Institute of Technology reaching the destination point within 48 h. Upon arrival, the seaweeds were quickly immersed for 2 days in a 400 L aquarium filled with water with a salt concentration of 3.5%.

PEF Treatment.

Figure 8A:
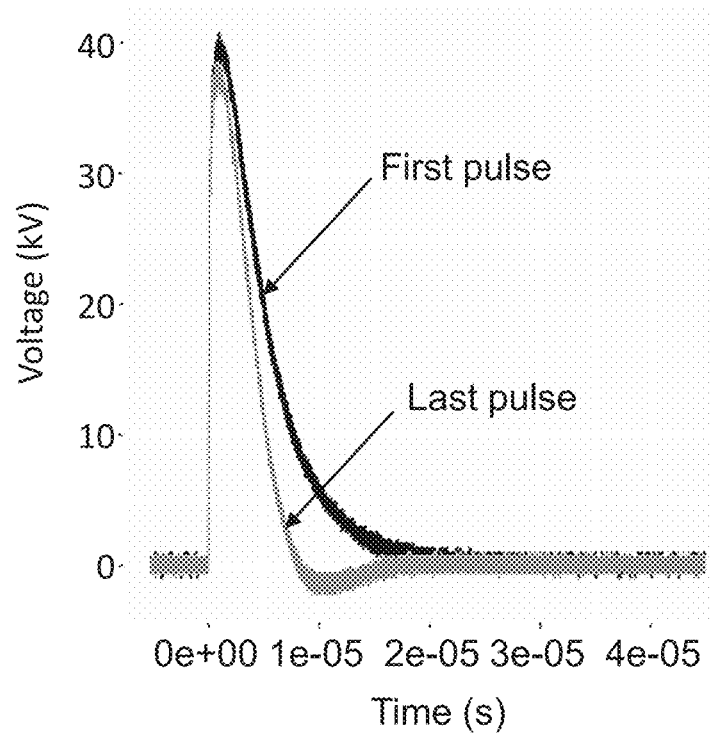
FIGS. 8A-8B show variation of the voltage during first and last pulses across the chamber (T1, 50 pulses of charging voltage 50 kV) (8A); and variation of the current during first and last pulses across the chamber (8B).

The fresh *Ulva rigida* biomass was centrifuged using a manual kitchen centrifuge for 3 runs of 1 min each to remove the external water, so that <1 g of water has been removed during the third run. About 140 g of *U. rigida* was loaded into the PEF treatment chamber with a volume of 232 $cm^3$ for the application of a homogeneously distributed PEF. The distance between the electrodes is 70.3 mm. Deionized water was added to the macroalgae to fill the chamber completely (<100 ml). Pressurizing the biomass in the chamber with water allowed to avoid the formation of air bubbles that could lead to malfunction. The treatment parameters were: charging voltage (0 to 50 kV) and pulses numbers (0 to 50) delivered at 0.5 Hz. The pulse duration was measured from the voltage measurement across the chamber (see below) and was defined as the length of time between the beginning of the pulse and when the voltage reaches the halftime amplitude. Duration varied between 4 and 6 µs (FIG. 8A). The temperature was measured with a digital thermometer (TFA Type 30.1018). Current and voltage across the electrodes of the treatment chamber during each pulse were measured with a current probe (PEARSON 110 A) and a voltage divider (HILO-Test HVT 240 RCR), both connected to an oscilloscope (Tektronix TDS 640A). The resistance of the treated sample was derived from the current and voltage measurements with Ohm's law.

The total energy consumed for the PEF treatment was calculated based on the energy stored in the pulse capacitor with the following Eq. 3:

$$E_t = 0.5 \times C \times (V)^2 \times N \qquad (Eq.3)$$

where $E_t$ (J) is the total energy consumed for the treatment, C is the discharging capacitor capacitance (F), V (V) is the applied voltage and N is the total number of pulses. Additional losses of the capacitor charger have not been considered. All combinations of charging voltage and number of pulses were applied on at least two replicates.

Mechanical Extraction of Internal Cell Content with Ash.

The PEF-treated biomass was placed in cloth material that was folded to prevent the algae from escaping during pressing. The algae wrapped up in the fabric were placed in the mechanical press (HAPA type SPM 2.5S). A force of 45 daN $cm^{-2}$ was applied for a determined time of 5 min using the automatic mode of the press that keeps the pressure applied to the piston constant. Extracted juice (called "juice") from pressing was collected in a 2 L beaker and weighted at the end of the pressing. The pressed material (called: "press-cake") was taken out of the press and weighted. Juices were collected and kept at −20° C. Cakes were spread on a plate and dried at 40° C. during 24 h, then kept at 5° C. Aliquot of the dried samples were then ground using liquid nitrogen, mortar, and pestle and then kept at −20° C. until analysis.

Dry Matter and Ash Content Measurements.

Juices samples (15±0.5 ml) and press-cake (0.5±0.01g) powder were weighted (m1=mass sample+crucible) and then dried at 105° C. using the conventional oven for 24 h in pre-weighted clean crucibles (m2=mass crucible). The crucibles were cooled down in a desiccator, weighted (m3), and ignited at 550° C. for 3h in a muffle furnace (Thermolyne muffle furnace, Thermo Scientific) and then cooled down to 105° C. The crucibles were finally removed from the furnace, kept in a desiccator to cool them down at room temperature and weighted (m4). The analysis was done in triplicate. Dry matter and ash content were calculated as shown in Eq. 4 and Eq. 5.

$$\text{dry matter content (\%)} = \frac{(m3 - m2)}{(m1 - m2)} \quad \text{(Eq. 4)}$$

$$\text{ash content (\%)} = \frac{(m4 - m2)}{(m3 - m2)} \quad \text{(Eq. 5)}$$

Element Analysis of Ash with Inductively Coupled Plasma—Optical Emission Spectrometry (ICP-OES).

A batch of ash sample (100 mg) was digested in 5 mL of $HNO_3$ 65%. Digestion was carried out in quartz vessels using a "Discover" sample digestion system at high temperature and pressure (CEM, USA). Vessels were cooled down and the volume was made up to 14 mL of deionized water. The samples were not dissolved completely but we assumed that the concentration of the elements was not impacted.

Element concentration was measured in the clear solutions using an axial ICP-OES model 'ARCOS' from Spectro GMBH, Germany Measurements were calibrated with standards for ICP from Merck, Germany Element concentrations that exceeded the linear dynamic range were diluted and reanalyzed. Dilution was made using calibrated pipettes. The continuing calibration verification standard was measured to check the instrument stability. Analyses were performed in the Interdepartmental Equipment Unit of the Hebrew University of Jerusalem in Rehovot, Israel.

Chlorine Analyses Cl Analyzer.

The aliquot of each press cake sample (about 250 mg) was mixed with 25 mL of deionized water in the polypropylene flask and then shaken at 250 rpm during 30 min. Then the sample was centrifuged (5000 rpm, 5 min) and Cl ion concentration was determined by "MK II Chloride Analyzer 926", Sherwood, UK. Liquid juices sample were directly analyzed after appropriate dilution. Analyses were performed in the Interdepartmental Equipment Unit of the Hebrew University of Jerusalem in Rehovot, Israel.

Statistics.

The results were analyzed by one-way analysis of variance (ANOVA) with significance level $\alpha=0.05$ followed, when applicable, with Tukey's multiple comparison tests. In some cases, Student's t-test was used instead of ANOVA when comparing only two treatments for each variable.

Results

PEF Ash Extraction Process Parameters

Figure 7:
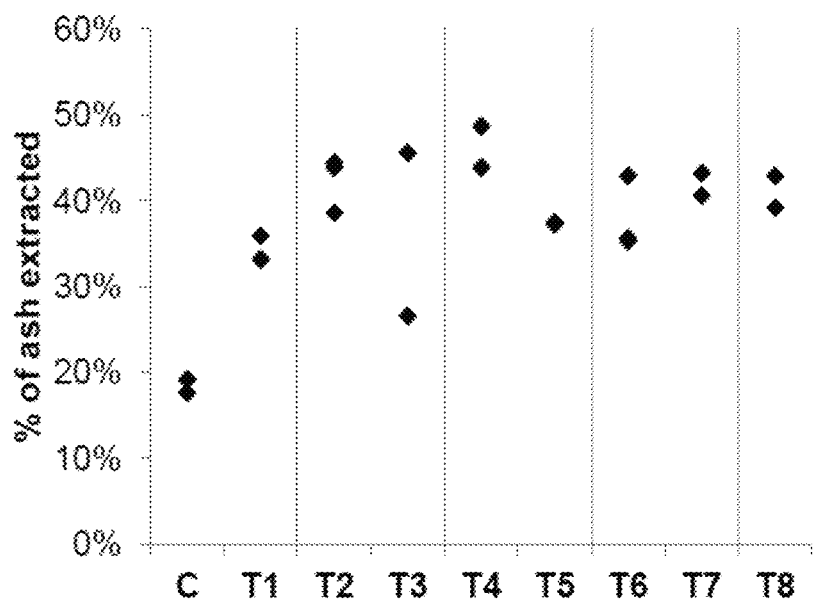
FIG. 7 shows the amount of ash extracted by mechanical pressing with and without PEF pretreatment, as described in Study 2.

To assess the effect of PEF on the deashing of seaweed biomass, the following steps were applied to the fresh seaweed biomass stored in salt water in an aquarium: harvesting, gentle dewatering, PEF treatment, hydraulic pressing and storage of the liquid extracts and the residual biomass. Samples only differed by the intensity of the PEF treatment applied in the chamber. In total, 8 different treatments were applied to different combinations of charging voltage (10, 20, 35 or 50 kV) and number of pulses (10, 20, 30, 40 and 50), as summarized in Table 5. A $9^{th}$ treatment where no electric field was applied (0kV, 0 pulses) served as control. Each treatment was replicated at least twice. As the control experiments were also put in deionized water, the osmotic shock that occurred was taking in the account and, therefore, we could attribute any difference only to the PEF treatment. FIG. 7 shows the amount of ash extracted by mechanical pressing in each one of the treatments vs. the control.

TABLE 5

The different PEF treatments applied

| Treatment | Sample# | Charging voltage (kV) | Number of pulses | Temperature after pulsing (° C.) | Total energy (kJ) |
|---|---|---|---|---|---|
| C | 8 | 0 | 0 | 27.1 | 0 |
| C | 20 | 0 | 0 | 27.9 | 0 |
| T1 | 18 | 20 | 50 | 36.7 | 6.0 |
| T1 | 19 | 20 | 50 | 35.3 | 6.0 |
| T2 | 13 | 35 | 50* | 45 | 18.4 |
| T2 | 14 | 35 | 50 | 46.2 | 18.4 |
| T2 | 15 | 35 | 50 | 44.1 | 18.4 |
| T3 | 16 | 35 | 10 | 31.2 | 3.7 |
| T3 | 17 | 35 | 10 | 32.1 | 4.7 |
| T4 | 9 | 50 | 20 | 43.5 | 13.8 |
| T4 | 10 | 50 | 20 | 42.4 | 13.8 |
| T5 | 11 | 50 | 10 | 34.7 | 6.9 |
| T5 | 12 | 50 | 10 | 34.4 | 6.9 |
| T6 | 1 | 50 | 50* | 66.6 | 34.6 |
| T6 | 2 | 50 | 50 | 67 | 34.6 |
| T6 | 3 | 50 | 50 | 69.7 | 34.6 |
| T7 | 4 | 50 | 40 | 60.6 | 27.6 |
| T7 | 5 | 50 | 40 | 59.3 | 27.6 |
| T8 | 6 | 50 | 30 | 49.7 | 20.7 |
| T8 | 7 | 50 | 30 | 49.6 | 20.7 |

First differences between treated samples and controls were observed during handling as they were hotter, sticky, and the juice obtained after pressing had a more intense greenish color. The initial temperature was around 27-28° C. and the final temperature was higher for all PEF treatments (31 to 70° C.). Part of the energy applied during PEF treatment is known to be released as heat under the Joule effect (Raso et al., 2016). The intensity of the Joule effect is obviously directly linked to the severity of the treatment, the higher the applied voltage and the number of pulses, the higher the energy released by Joule effect and thus the higher the final temperature. This, however, needs to be kept in mind while analyzing results, as the temperature is a key parameter of many physicochemical phenomena such as molecule diffusion in a liquid matrix (Vorobiev and Lebovka, 2009).

Figure 8B:
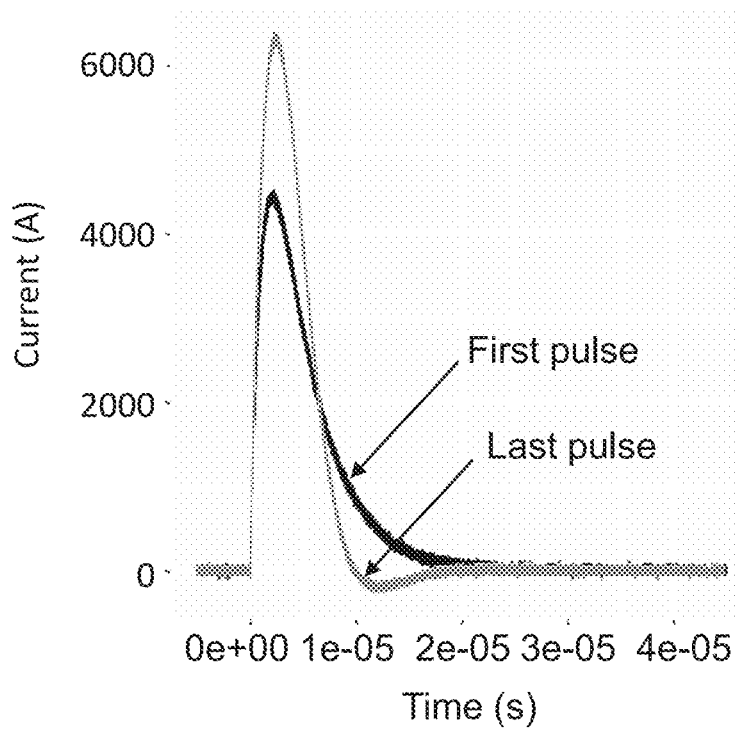

The shapes of pulses obtained from voltage measurement at the chamber were mainly due to the design of the pulse generator (sparkgap, etc.). However, a decrease in measured voltage, as well as slight differences in pulse shape, were monitored throughout the treatments. Those differences were maximum between the first and last pulses of each treatment as seen in FIG. 8. In parallel with the voltage slightly decreasing, an increase in the current in the chamber was observed as well (Table 6). This phenomenon is linked to the decreasing of the resistance inside the chamber as intracellular components such as ions are released during electroporation leading to decrease of the resistance inside the chamber. This observation is commonly observed during electroporation (Bluhm and Sack, 2008; Polikovsky et al., 2016). Drops between initial and final resistances for all treatments were in the range of 2-7 Ω. The voltage amplitudes measured at the chamber were smaller than the charging voltage set on the pulse generator, this is caused by the inductance of the capacitor discharging circuit and is a common characteristic of capacitor discharge circuits and is due to the design of the pulse generator as well as the resistance of the chamber (Raso et al., 2016).

TABLE 6

Evolution of the maximum voltage, current, and resistance of the chamber between the first and the last pulses

|  | Max voltage Umax (kV) | Max current Imax (A) | Resistance R R = Umax/Imax (Ω) |
|---|---|---|---|
| First pulse | 40.68 | 4528 | 8.98 |
| Lat pulse | 38.44 | 6384 | 6.02 |

At all applied electric fields (from 2 to 6 kV/cm), the biomass was permeabilized, which is confirmed by resistance decreasing during the treatment. Electroporation of seaweed cell in such condition is expected as the threshold to induce permeabilisation of the membrane is linked to the cell size with the usual following correlation: the bigger the cell, the lower the voltage threshold (Kotnik et al., 2012). In the conditions of our experiments, we were above that threshold, and thus this could expect the relatively similar results obtained for most applied treatments. For the more severe treatments (higher number of pulses and/or higher charging voltage), the extra-heating from the Joule effect could have led to differences between the 8 treatments, notably due to thermo-induced damages or the quicker diffusion of molecule out of the seaweed matrix; however, the hydraulic press step would have made this observation hard to monitor.

Dry Matter and Ash Contents Analysis of Liquid PEF Extracts and Residual Biomass The average dry matter content of liquid extracts (reflecting the amount of materials extracted) was 3.8% (min=2.9% and max=5.7% for T2 (35 pulses of 50kV) and T6 (50 pulses of 50 kV) respectively, Table 7) of the juice weight for PEF-treated samples compared to 2% for the control samples (min=1.7%, max=2.3%, Table 7). Of this dry matter, a considerable amount was found to be ashes (82.5±3.0% for controls and 72.1±1.2% for PEF-treated samples, the difference was not significant). The ash contents per mass of juice were 2.76 (min=2.07%; max=3.94%, for T2 (35 pulses of 50 kV) and T6 (50 pulses of 50 kV, respectively)) and 1.65% (min=1.48%, max=1.82) for PEF-treated samples and control, respectively (Table 7). ANOVA analysis showed that there were significant differences in both dry matter and ash content (ANOVA p-value=0.028 and 0.00004 respectively). Subsequent post hoc tests (pair-wise test) demonstrate that most PEF treatments had significantly different dry matter and ash contents (but 3 treatments: T2, T7 (40 pulses of 50 kV) and T8 (30 pulses of 50 kV)) compared to control experiments. Interestingly, PEF treatments were not statistically different from each other for both dry and ash content with the exception of the results of treatment T6, which had significantly different dry matter and ash contents compared to the treatments T2, T7, and T8. In other words, the PEF-assisted extraction process extracted more ash into the liquid juice compared to pressing alone in a significant manner in 5 over 8 treatments. And if a relatively wide range of results was found between the dry matter and the ash content of liquid extracts of the different PEF-treated samples (Table 7), only a few were significantly different from others.

This was confirmed by the analysis of the ash remaining in the residual biomass. The average ash contents of the residual biomass were 20.63% (min=17.81, max=24.88, for T7 (40 pulses of 50 kV) and T3 (10 pulses of 35 kV), respectively) for the PEF-treated samples and 26.1% (min=25.75, max=26.45) for the control (Table 7). Significant differences among the different treatments were found following ANOVA analysis on the ash content of the residual biomass (p-value=0.023). The following pair-wise comparison confirms that the ash content of residual biomass of all PEF-treated groups was significantly different from the ash content of the residual biomass of the control group. Once again, no significant differences were found between the ash content of the residual biomass of the different PEF-treated samples (but for T3 and T1 (50 pulses of 20 kV) with T7).

Figure 9A:
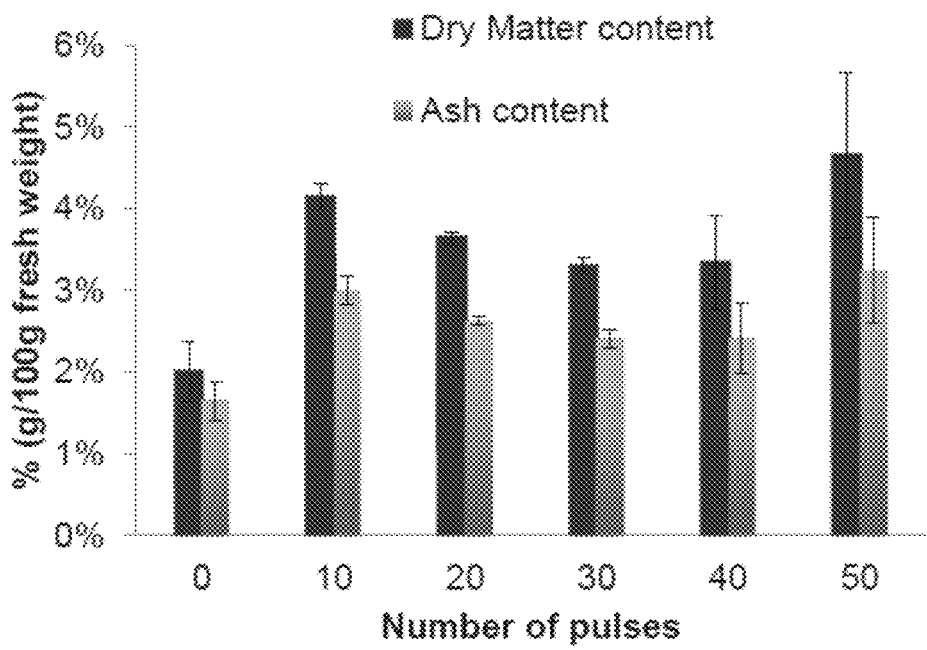
FIGS. 9A-9D show effect of pulse number and charging voltage on dry matter content and ash content of the liquid extract (9A and 9B), and the ash content of the residual biomass (9C and 9D). Results are expressed as mean of duplicates while error bar show standard deviation. Analyses of the variance show that both pulse number and charging voltage had an effect on those three parameters (dry matter and ash content of liquid extracts, ash content of residual biomass) ($p<0.05$). (DM—dry matter).
Figure 9B:
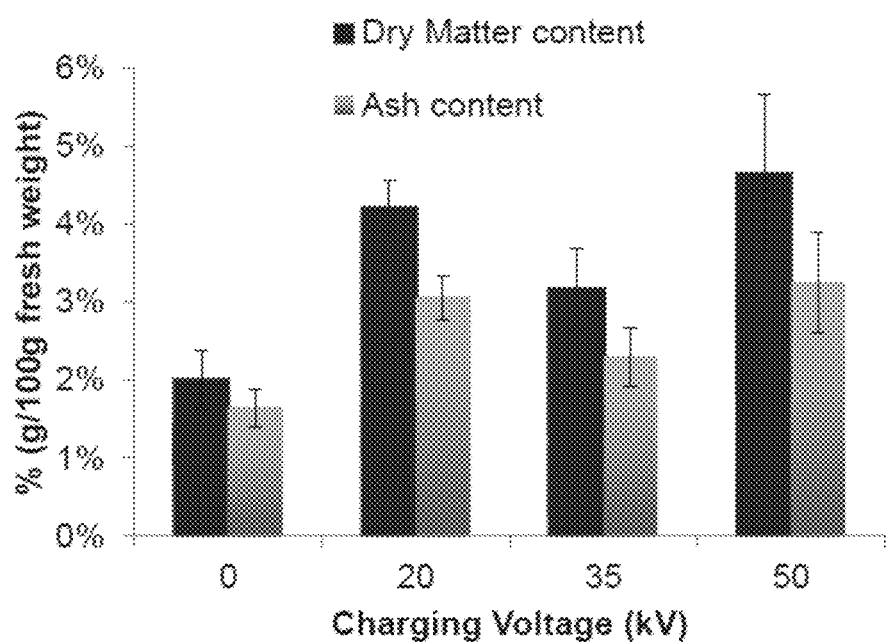
Figure 9C:
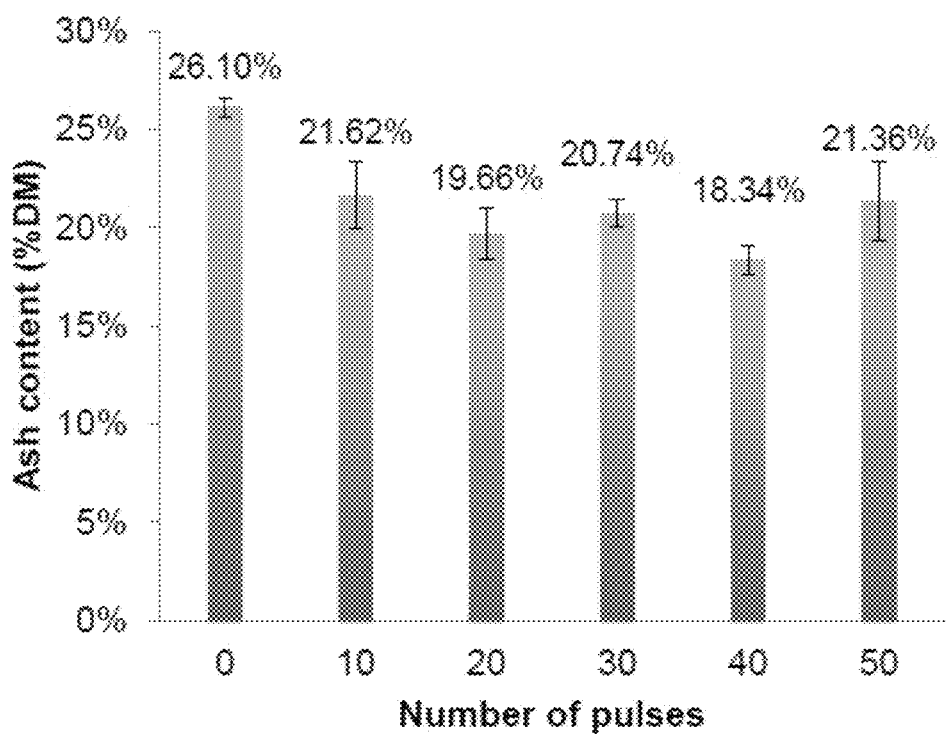
Figure 9D:
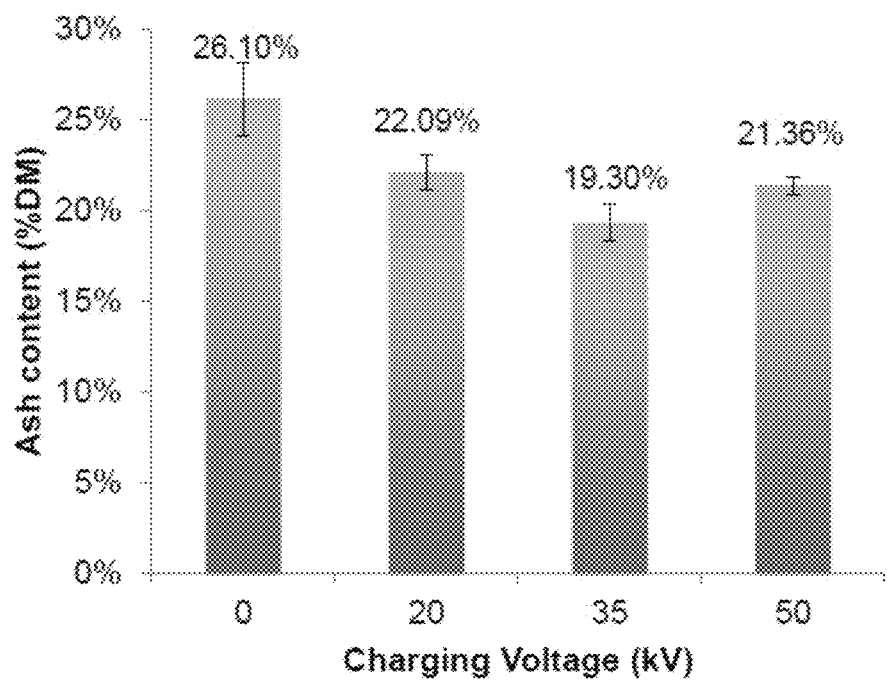
Figure 10A:
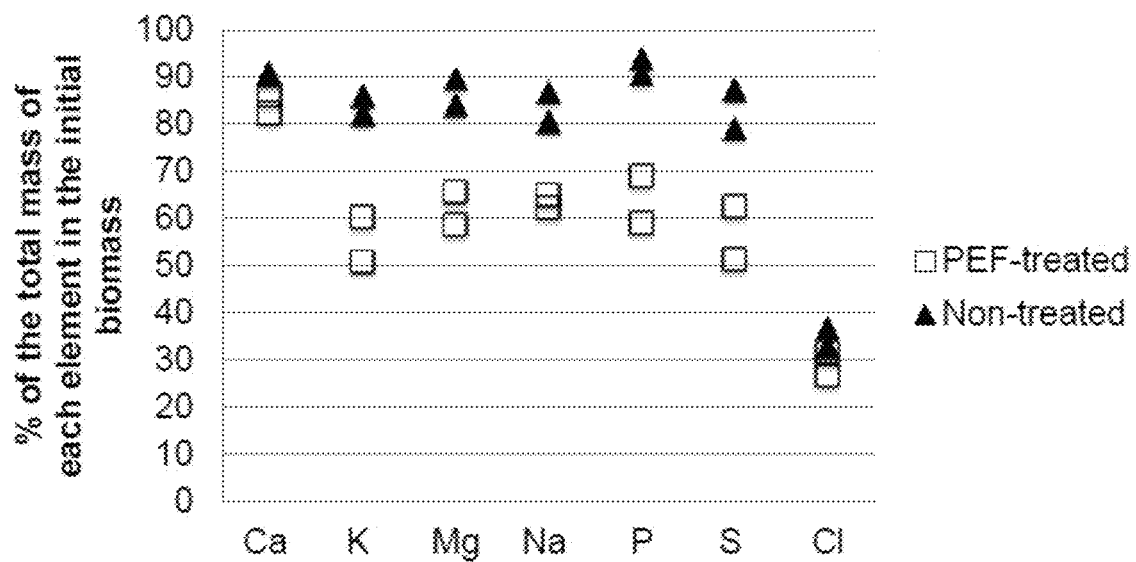
FIGS. 10A-10B show fractions of the main ash elements (elements that made 1% or more of the total ash content) extracted in the residual biomass (10A) or remaining in treated and non-treated seaweed extracted juices (10B) after hydraulic press, as % of the mass of the element in the initial biomass.
Figure 10B:
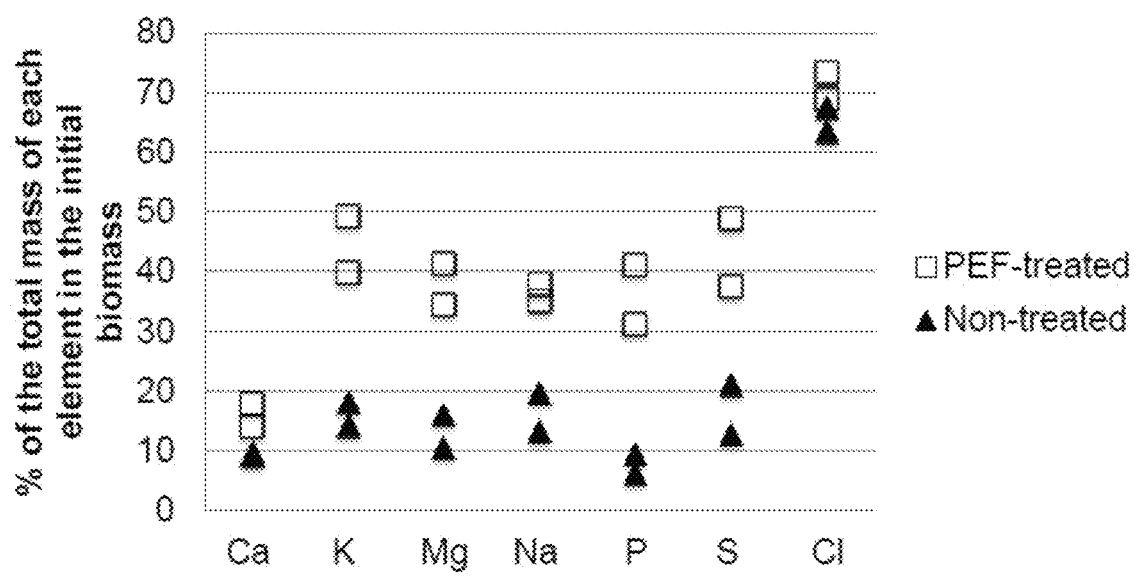

FIGS. 9A and 9B show the effect of a different number of pulses applied with the same charging voltage (50 kV) on dry matter and ash content of the liquid extract (9A) and the ash remaining in the residual biomass (9C). FIGS. 10B and 10D show dry matter and ash content of the liquid extract (10B) and the ash remaining in the residual biomass (10D) for treatments of 50 pulses of the different charging voltage. There was no visible trend showing an improvement of ash extraction with treatment severity (increase in a number of pulses and/or charging voltage). Moreover, the profile of the ash contents of the liquid extracts was not visibly correlated with the profile of the amount of ash in the residual biomass of the same samples, we, therefore, believe that this difference between treatments could be attributed to the process conditions, the recovery and the storage of samples.

Total ash content of the initial materials was calculated from the sum of ash extracted plus the remaining ash, the average value was 29±0.1% of the dry matter. From those values, the fractions of ash extracted through the applied process were showed in FIG. 7. For the control experiment, less than 20% of the initial ash was extracted (18.4±1.1%), whereas for PEF-treated samples, 27-49% of the initial ash were extracted with an average value of 39.7±5.3%, which is a two-fold increase.

These results show, for the first time, that PEF could enhance ash extraction directly from freshly harvested biomass when coupled with mechanical pressing. When an electric field was applied, permeabilization of the cell helped the extraction of ash by hydraulic pressing leading to a two-fold increase compared to pressing alone as mentioned above. No major differences were observed between the different PEF treatment conditions thus we advise using the treatment with the lowest energy expenditure in order to reduce energy expenditure. Further work would be needed to assess the minimum treatment allowing the permeabilization of seaweed cell, as working in such conditions would save energy, reduce processing cost and thermal damage to biomass constituents. Nevertheless, parameters of minimum required treatments such as voltage threshold highly depend on the process conditions and the type of the biomass (Haberl et al., 2013; Kotnik et al., 2012) and should be tuned accordingly, on a case by case basis.

Removal of around 40% of the initial ash content could be a key step to enhance the value of the biomass for, e.g., energy, animal feed, and human consumption. Notably, analysis of the liquid extract shows that the major party of the extracted dry matter was ash (>70%, see Table 7), thus only a small amount of organic compounds was extracted. This selectivity toward ash could be explained by the small size of salts that could easily diffuse through the pore of the membrane (Haberl et al., 2013; Kotnik et al., 2012). However, one needs to keep in mind that a fraction of the ash content could also be included in organic molecules such as protein or polysaccharide. In *Ulva* sp. for example, the polysaccharide ulvan is the major constituent of the cell wall (Robic et al., 2009). This polysaccharide is a sulfated polysaccharide thus containing an appreciable amount of ash bond to its organic skeleton as a sulfated group. Thus, extraction of valuable organic molecules containing metals or other ash elements could still occur. In any case, the ratio of ash over an organic matter of 70/30 makes the loss of valuable organic molecules such as protein or polysaccharide negligible. In addition, low severity PEF-treatment lead to a temperature increased of the biomass of only few degrees Celsius while most of the treatment applied in this work did not warm the biomass over 50° C., thus preserving most of its thermo-sensitive constituents.

TABLE 7

Dry matter and ash contents of liquid extract and residual biomass of the different samples and treatments (FW = fresh weight, DM = dry matter).

| Sample n° | Treatment n° | Liquid extract | | | Residual biomass |
|---|---|---|---|---|---|
| | | DM | Ash (% FW) | Ash (% DM) | Ash (% DM) |
| 1 | T6 | 5.75% | 3.94% | 68.50% | 19.17% |
| 2 | T6 | 3.75% | 2.66% | 70.81% | 21.74% |
| 3 | T6 | 4.46% | 3.15% | 70.78% | 23.17% |
| 4 | T7 | 2.93% | 2.11% | 71.98% | 17.81% |
| 5 | T7 | 3.74% | 2.71% | 72.55% | 18.87% |
| 6 | T8 | 3.38% | 2.49% | 73.77% | 20.26% |
| 7 | T8 | 3.24% | 2.32% | 71.69% | 21.23% |
| 8 | C | 2.26% | 1.82% | 80.38% | 25.75% |
| 9 | T4 | 3.58% | 2.60% | 72.45% | 20.57% |
| 10 | T4 | 3.69% | 2.66% | 72.12% | 18.75% |
| 11 | T5 | 4.27% | 3.12% | 73.13% | 20.41% |
| 12 | T5 | 4.04% | 2.87% | 71.17% | 22.82% |
| 13 | T2 | 3.77% | 2.73% | 72.36% | 20.41% |
| 14 | T2 | 2.88% | 2.10% | 72.93% | 18.68% |
| 15 | T2 | 2.87% | 2.07% | 72.20% | 18.80% |
| 16 | T3 | 3.46% | 2.51% | 72.43% | 19.58% |
| 17 | T3 | 4.99% | 3.57% | 71.47% | 24.88% |
| 18 | T1 | 4.46% | 3.25% | 72.98% | 22.81% |
| 19 | T1 | 3.94% | 2.86% | 72.41% | 21.36% |
| 20 | C | 1.74% | 1.48% | 84.69% | 26.56% |

Element Analysis of Liquid Extracts and Residual Biomass

In order to get a more detail insight of the ash extraction process by PEF treatment followed by the hydraulic press, we analyzed the ash composition of both the liquid extract and the residual biomass of selected experiments. The two controls were therefore chosen to be compared with experiment 1 and 2, which were subject to the most severe treatment (T1, 50 pulses of charging voltage 50 kV).

Results from ICP-OES analysis show that the main elements, in decreasing order, in the seaweed ash were S, Cl, Mg, Na, K, Ca, and P, which account for 25.3±1.15%, 21.37±1.12%, 18.51±0.96%, 13.32±1.13%, 11.47±0.91%, 8.66±2.00%, and 1.08±0.05% of the crude ash, respectively, which is a common profile for such seaweed (Bikker et al., 2016). Other trace elements such as Al, Cd, Co, Cr, Ni, Ti, Zn, Fe, Cu, Mn, and Si were also monitored. Some elements were not found or their concentration was below the equipment threshold (such as Pb, As, Bis, Hg, Mo, Se, Sb, W, and Au), therefore, they were not displayed. Concentrations of major (>1% of total ash) and traces (<1% of total ash) were then correlated with the mass of liquid extracts and residual biomass obtained after pressing (data not shown) to determine the fraction of each element that was extracted and the fraction that remains in the residue. The results are shown in Table 8. Traces elements such as Cd, Cu, Fe or Cr had a very high standard deviation between the two duplicates for each experiment, which was attributed to their very low value (less than 1% of the total ash content).

Osmotic shock followed by mechanical pressing was able to extract an average value of 18.2±14.0% of each element; with a maximum value of 65.3% for Cl and a minimum value of 4.7% for Zn. PEF-assisted deashing was able to extract an average value of 29.3±17.8% for each element; with a maximum value of 71.0% for Cl and a minimum value of 4.7% for Fe (Table 8).

Among all elements presented in Table 8, only K (44.43±6.72% vs. 16.04±2.75%), Mg (37.8±4.89% vs. 13.22±3.97%), Na (36.37±1.96% vs. 16.4±4.44%), Ni (22.8±3.8% vs. 10.01±2.99%), P (36.04±7.03% vs. 7.72±2.25%), S (43.11±8.04% vs. 16.84±5.8%) and Zn (7.38±0.79% vs. 4.74±0.71%) were significantly affected by the PEF-pretreatment. Those seven elements were extracted in a higher amount for the PEF-treated samples compared to the control, showing certain selectivity in the ash extraction compared to simple mechanical pressing. Moreover, five of those seven elements (K, Mg, Na, P, and S) were considered as a major element (>1% of total ash) supporting the use of PEF to successfully enhance major ash element extraction from biomass.

Interestingly, pressing alone was sufficient to remove more than 60% of the Cl initial content, and PEF did not significantly influence the extraction of this major element although it slightly improved it (see Table 8). Cl ions are therefore easily extractable from seaweed biomass with water washing and mechanical pressing, which is due to the fact that their presence is mainly due to residual seawater containing a high level of NaCl. In an opposite fashion, Ca, was the only major element that was hardly extracted with PEF-assisted mechanical pressing (15.87±2.72% extracted) and with mechanical pressing alone (9.37±0.42% extracted). We make the hypothesis that those Ca ions (as well as Zn and Fe, that were also poorly extracted) might be trapped by ionic or weak interactions with charged molecules such as a sulfated polysaccharide (Chiellini and Morelli, 2011).

Only three elements were extracted in lower amount when PEF-treatment was applied, this is the case for Fe, Ti, and Si, but there were no significant differences between control and PEF-treated samples (see Table 8).

TABLE 8

Amount of the main elements in the ash of the residual biomass and the liquid extract obtain by hydraulic-pressing of PEF-treated and non-treated (CTRL = control who was osmotic shock treated only) seaweed samples.

| | Residual biomass | | Liquid extract | | |
|---|---|---|---|---|---|
| Element | PEF | CTRL | PEF | CTRL | p value |
| Al | 80.88 ± 12.05 | 81.97 ± 2.29 | 19.13 ± 12.05 | 18.04 ± 2.29 | 0.46 |
| Ca | 84.14 ± 2.72 | 90.64 ± 0.42 | 15.87 ± 2.72 | 9.37 ± 0.42 | 0.09 |
| Cd | 53.93 ± 29.71 | 71.68 ± 23.06 | 46.08 ± 29.71 | 28.33 ± 23.06 | 0.29 |
| Cr | 85.73 ± 2.32 | 86.51 ± 12.89 | 14.28 ± 2.32 | 13.5 ± 12.89 | 0.48 |
| Cu | 53.27 ± 6.1 | 67.14 ± 32.97 | 46.74 ± 6.1 | 32.87 ± 32.97 | 0.33 |

TABLE 8-continued

Amount of the main elements in the ash of the residual biomass and the liquid extract obtain by hydraulic-pressing of PEF-treated and non-treated (CTRL = control who was osmotic shock treated only) seaweed samples.

| Element | Residual biomass | | Liquid extract | | p value |
|---|---|---|---|---|---|
| | PEF | CTRL | PEF | CTRL | |
| Fe | 95.34 ± 0.3 | 87.33 ± 13.2 | 4.67 ± 0.3 | 12.68 ± 13.2 | 0.28 |
| K  | 55.58 ± 6.72 | 83.97 ± 2.75 | 44.43 ± 6.72 | 16.04 ± 2.75 | 0.04 |
| Mg | 62.21 ± 4.89 | 86.79 ± 3.97 | 37.8 ± 4.89 | 13.22 ± 3.97 | 0.02 |
| Mn | 75.01 ± 2.01 | 89.07 ± 8.47 | 25 ± 2.01 | 10.94 ± 8.47 | 0.13 |
| Na | 63.64 ± 1.96 | 83.61 ± 4.44 | 36.37 ± 1.96 | 16.4 ± 4.44 | 0.04 |
| Ni | 77.21 ± 3.8 | 90 ± 2.99 | 22.8 ± 3.8 | 10.01 ± 2.99 | 0.04 |
| P  | 63.97 ± 7.03 | 92.29 ± 2.25 | 36.04 ± 7.03 | 7.72 ± 2.25 | 0.05 |
| S  | 56.9 ± 8.04 | 83.17 ± 5.8 | 43.11 ± 8.04 | 16.84 ± 5.8 | 0.04 |
| Si | 83.09 ± 3.1 | 79.69 ± 0.52 | 16.92 ± 3.1 | 20.32 ± 0.52 | 0.18 |
| Ti | 88.18 ± 1.16 | 86.51 ± 12.89 | 11.83 ± 1.16 | 13.5 ± 12.89 | 0.45 |
| Zn | 92.36 ± 0.79 | 95.27 ± 0.71 | 7.38 ± 0.79 | 4.74 ± 0.71 | 0.04 |
| Cl | 28.99 ± 3.23 | 34.67 ± 2.89 | 71.02 ± 3.23 | 65.34 ± 2.89 | 0.11 |

\* Results are expressed as mean (%) of duplicate ± stdev. P-values were obtained from Tukey t-test between the treated and non-treated sample, bold values are the significant values (<0.05)

Finally, there are few missing elements (nitrogen and iodine) that could not be monitored using Cl-analyzer and ICP-OES and whom fate could be of major importance. The first one, N, has a key role as a major nutrient for plants (Carey et al., 2016), whereas I is of crucial interest for its impact (positive or negative) on human health (Zimmermann, 2009). Additional work incorporating those two elements as well as others could fill such gap and contribute to the understanding and the application of PEF-assisted deashing step.

Comparisons with Previous Works to Enhance Biofuel Productions by Biomass Deashing The results provided herein show that PEF was improving the extraction of almost all elements, notably most of the major seaweed ash elements (K, Mg, P, Na and S) when using to pre-treat biomass prior to mechanical pressing. Not only PEF was able to improve the ash extraction, but our proposed process can be directly applied on freshly harvested biomass. Thus, it could be easily integrated, as a first unitary operation, in biomass processing lines or directly on the harvesting site.

This is critical, because if the deashing operation prior to processing was shown to improve biomass uses to produce energy and fuel by thermochemical or biological means (Chen et al., 2014; He et al., 2014; Hu et al., 2017; Huang et al., 2016; Kang et al., 2011; Pattiya et al., 2013; Stefanidis et al., 2015), the industrial and environmental relevance of such operation are not always considered. For example, deashing of corn stover as described in He et al. (2014), showed that an ash reduction of 51% (from 9.60 to 4.98% ash), improved the hydrolysis yield 1.6 time (from 43.30 to 70.99%) and the ethanol yield 1.4 time (from 51.74 to 73.52%) (He et al., 2014). However, the results mentioned above were the maximum results obtained after the biomass was washed with an amount of water corresponding to 100 times the weight of biomass. In another work, a similar deashing strategy was used on seaweed biomass (washing with a ratio of 1:100 w/w of water during 12h) and decreasing in K (78%), Ca (5%), Na (74%) and Mg (54%) were reported (Hu et al., 2017). These values are higher than the ones obtained in this work (except for Ca, confirming the difficulty of its removal from seaweed biomass with water alone) however, one need to note that using such amount of water and time is not easily integrated with biomass processing, and potential microbial growth that can occur during that lapse of time and the tremendous amounts of water that need to be handled afterward. In this same study, different acids treatments (with HCl, $H_2SO_4$, and $H_3PO_4$) were also investigated. In almost all cases, the ash removal was almost complete (<90% reduction in K, Ca, Na and Mg in most case), but the usage of strong acids (7 or 10% solution) with a solid to volume ratio of 1:100 is not likely to be easily integrated in biorefineries, notably when considering that the biomass was then washed again with water to remove the acid. Moreover, loss of organic compounds was reported, and although it was not clear how much of the organic content in the biomass was lost, it is obvious that strong acid treatment for such time will degrade a considerable amount of sensitive materials and should not be considered when targeted products are acid sensitive. Nevertheless, this study shows significant removal of Ca using a strong acid, which confirms the presence of weak interactions between Ca and other biomass components, and give a viable option for Ca removal.

Another study (Chen et al., 2014) focus on deashing microalgae from wastewater using water and centrifugation. A maximum of 35% ash reduction was obtained (from 28.6% to 18.6% which are values similar to those shown in this work) and yield of crude bio-oil obtained from deashing algal biomass was improved. But the scalability and the integration of the suggested deashing process can be questioned again considering its complexity as the fresh biomass they used was washed a first time with water (1 h), dried, grinded, divided by screening, suspended in water (5% w/v ratio), centrifuged, re-suspended (5% w/v ratio) and re-centrifuged for a total processing time superior to 1h. In our work, we obtained similar results on seaweed biomass by removal of surface water, PEF-treatment, and mechanical pressing, which were quicker (less than 10 min) and used less water than all studies mentioned above (less than 100 ml of water was added to 140 g of fresh seaweed biomass containing about 26 g of dry matter). Additionally, if a batch process was used in our study, continuous processing can be considered, as continuous PEF devices are already available at industrial scale (Bluhm and Sack, 2008).

PEF-assisted deashing has therefore considerable advantages that when put into balance with current solutions can make it a promising technology for deashing fresh biomass as it is easily scalable (Bluhm and Sack, 2008), it is a food grade technology (Mahnič-Kalamiza et al., 2014), mild thermal (Kotnik et al., 2015; Mahnič-Kalamiza et al., 2014), do not use any chemical addition (Kotnik et al., 2015; Mahnič-Kalamiza et al., 2014), quick (few minutes in this work) (Bluhm and Sack, 2008; Golberg et al., 2016), and with an energy and water consumptions relatively low (Golberg et al., 2016; Sack et al., 2010b). Optimization of the process itself such as applying a second washing and pressing step and tuning the PEF-treatment could further improve the ash extraction yield and reduce the energy consumption, respectively.

Relevance for Other Biomass Processing

The ash content of biomass such as seaweed can be detrimental to their uses as feed for livestock; thus, deashing biomass could improve their nutritional value (Makkar et al., 2016). Notably, high ash content limits their inclusion into the diet of common livestock as it reduces the feed energy value and can provide some mineral in excess (Evans and Critchley, 2014; Makkar et al., 2016).

Ash extracts are usually of less value than the residual biomass, yet, it still contains valuables nutrients that are essential to biomass productions and the key to the development of sustainable biorefineries (Carey et al., 2016). Thus, the recycling of part of the nutrients such as P or K is of major interests for the development of future biorefineries as it can be recycled for biomass production. In our case, such nutrients can be re-used in seagriculture, but also for traditional land agriculture where seaweed and seaweed extract have been used as fertilizer for a century and are currently a booming sector (Craigie, 2011).

Finally, the removal of ash, as well as water, would improve the supply chain for future biorefineries, as "useless" weight would be removed before transport to the processing plant, saving the precious amount of transport fuels. Moreover, lower ash content means higher organic content in the residual biomass (higher carbohydrate, higher protein etc.), increasing the value of the residual biomass and improving subsequent processing steps in general.

Conclusions

PEF treatment (10-50 pulses of 10-50 kV) followed by hydraulic pressing was able to drastically increase the extraction yield of ash from fresh seaweed biomass leading to the extraction of 39.7±5.3% of the initial ash content compared to 18.4±1.1% for hydraulic pressing alone. PEF treatment could therefore be used as a quick, water efficient, energy efficient, scalable, continuous or discontinuous, mild thermal and non-chemical pretreatment for deashing biomass without significantly impacting its valuable constituents. The proposed pretreatment is particularly promising for ash removal, nutrient recovery and dewatering of biorefinery feedstock, notably of the marine source.

REFERENCES

Barbarino E, Lourenço S O. An evaluation of methods for extraction and quantification of protein from marine macro- and microalgae. *J. Appl. Phycol.*, 2005, 17(5), 447-460

Bikker P, Krimpen M M, Wikselaar P, Houweling-Tan B, Scaccia N, Hal J W, Huijgen W J, Cone J W, López-Contreras A M, Biorefinery of the green seaweed *Ulva lactuca* to produce animal feed, chemicals and biofuels. *Journal of Applied Phycology*, 2016, 1-15

Bluhm H, Sack M. Industrial-scale treatment of biological tissue with pulsed electric fields. in *Electrotechnologies for Extraction from Food Plants and Biomaterial*, E. Vorobiev and N Lebovka Eds. Springer Science and Business Media LLC, 2008, 237-269

Carey D E, Yang Y, McNamara P J, Mayer B K, Recovery of agricultural nutrients from biorefineries. *Bioresource Technology*, 2016, 215, 186-198

Chen W T, Ma J, Zhang Y, Gai C, Qian W, Physical pretreatments of wastewater algae to reduce ash content and improve thermal decomposition characteristics. *Bioresource Technology*, 2014, 169, 816-820

Chiellini F, Morelli A, Ulvan: a versatile platform of biomaterials from renewable resources. 2011, *INTECH Open Access Publisher*

Coustets M, Joubert-Durigneux V, Hérault J, Schoefs B, Blanckaert V, Garnier J.-P, Teissié J. Optimization of protein electroextraction from microalgae by a flow process. *Bioelectrochemistry*, 2015, 103, 74-81

Craigie J S, Seaweed extract stimuli in plant science and agriculture. *Journal of Applied Phycology*, 2011, 23(3), 371-393

Doevenspeck H. Influencing cells and cell walls by electrostatic impulses. *Fleishwirtshaft*, 1961, 13, 986-987

Evans F D, Critchley A T, Seaweeds for animal production use. *Journal of Applied Phycology*, 2014, 26(2), 891-899

Fleurence J, Le Coeur C, Mabeau S, Maurice M, Landrein A. Comparison of different extractive procedures for proteins from the edible seaweeds *Ulva rigida* and *Ulva rotundata*. *J. Appl. Phycol.*, 1995, 7(6), 577-582

Fleurence J. *Proteins in Food Processing*. Elsevier, 2004

Friedlander M, Israeli R & D activities in seaweed cultivation. *Israel Journal of Plant Sciences*, 2008, 56(1-2), 15-28

Galland-Irmouli A V, Pons L, Luçon M, Villaume C, Mrabet N T, Guéant J L, Fleurence J. One-step purification of R-phycoerythrin from the red macroalga *Palmaria palmata* using preparative polyacrylamide gel electrophoresis. *Journal of Chromatography B: Biomedical Sciences and Applications*, 2000, 739(1), 117-123

Ganeva V, Galutzov B. Electropulsation as an alternative method for protein extraction from yeast. *FEMS Microbiol. Lett.*, 1999, 174(2), 279-284

Ganeva V, Galutzov B, Teissié J. High yield electroextraction of proteins from yeast by a flow process, *Anal. Biochem.*, 2003, 315(1), 77-84

Goettel M, Eing C, Gusbeth C, Straessner R, Frey W. Pulsed electric field assisted extraction of intracellular valuables from microalgae. *Algal Res.*, 2013, 2(4), 401-408

Golberg A, Rubinsky B. The effect of electroporation type pulsed electric fields on DNA in aqueous solution, *Technol. Cancer Res. Treat.*, 2010, 9(4), 423-430

Golberg A, Broelsch G F, Bohr S, Mihm M C, Austen W G, Albadawi H, Watkins M T, Yarmush M L. Non-thermal, pulsed electric field cell ablation: A novel tool for regenerative medicine and scarless skin regeneration. *Technology*, 2013, 1(1), 1-8

Golberg A, Sack M, Teissie J, Pataro G, Pliquett U, Saulis G, Stefan T, Miklavcic D, Vorobiev E, Frey W, Energy-efficient biomass processing with pulsed electric fields for bioeconomy and sustainable development. *Biotechnology for biofuels*, 2016, 9(1), 94

Haberl S, Miklavcic D, Sersa G, Frey W, Rubinsky B, Cell membrane electroporation-Part 2: the applications, 2013

Haberl Meglic S, Marolt T, Miklavcic D. Protein extraction by means of electroporation from *E. coli* with preserved viability. *J. Membr. Biol.*, 2015

Harnedy P A, FitzGerald R J. Bioactive proteins, peptides, and amino acids from macroalgae. *J. Phycol.*, 2011, 47(2), 218-32

Harnedy P A, FitzGerald R J. Extraction of protein from the macroalga *Palmaria palmate*. *LWT-Food Sci. Technol.*, 2013, 51(1), 375-382

He Y, Fang Z, Zhang J, Li X, Bao J, De-ashing treatment of corn stover improves the efficiencies of enzymatic hydrolysis and consequent ethanol fermentation. *Bioresource Technology*, 2014, 169, 552-558

Hu Y, Wang S, Wang Q, He Z, Lin X, Xu S, Ji H, Li Y, Effect of different pretreatments on the thermal degradation of seaweed biomass. *Proceedings of the Combustion Institute*, 2017, 36(2), 2271-2281

Huang C, Wu X, Huang Y, Lai C, Li X, Yong Q, Prewashing enhances the liquid hot water pretreatment efficiency of waste wheat straw with high free ash content. *Bioresource Technology*, 2016, 219, 583-588

Joubert Y, Fleurence J. Simultaneous extraction of proteins and DNA by an enzymatic treatment of the cell wall of *Palmaria palmata* (Rhodophyta). *J. Appl. Phycol.*, 2007, 20(1), 55-61

Kang L, Wei W, Pallapolu V R, Lee Y Y, Enhanced ethanol production from de-ashed paper sludge by simultaneous saccharification and fermentation and simultaneous saccharification and co-fermentation. *BioResources*, 2011, 6(4), 3791-3808

Kotnik T, Kramar P, Pucihar G, Miklavcic D, Tarek M, Cell membrane electroporation-Part 1: The phenomenon. *IEEE Electrical Insulation Magazine*, 2012, 28(5), 14-23

Kotnik T, Frey W, Sack M, Haberl Meglič S, Peterka M, Miklavčič D. Electroporation-based applications in biotechnology. *Trends Biotechnol.*, 2015, 33(8), 480-488

Krupnik N P G, Douek J, Lewinshohn E, Israel A, Mineur F, Maggs C, In Press. Native and invasive *Ulva* species from the Israeli Mediterranean Sea: risk and potential. *Mediterr. Mar. Sci.*

Mahnič-Kalamiza S, Vorobiev E, Miklavčič D, Electroporation in food processing and biorefinery. *The Journal of Membrane Biology*, 2014, 247(12), 1279-1304

Makkar H P S, Tran G, Heuzé V, Giger-Reverdin S, Lessire M, Lebas F, Ankers P, Seaweeds for livestock diets: A review. *Animal Feed Science and Technology*, 2016, 212, 1-17

Ohshima T, Tamura T, Sato M. Influence of pulsed electric field on various enzyme activities. *J. Electrostat.*, 2007, 65(3), 156-161

Parniakov O, Barba F J, Grimi N, Marchal L, Jubeau S, Lebovka N, Vorobiev E. Pulsed electric field and pH assisted selective extraction of intracellular components from microalgae Nannochloropsis. *Algal Res.*, 2015, 8, 128-134

Pattiya A, Chaow-u-thai A, Rittidech S, The Influence of pretreatment techniques on ash content of cassava residues. *International Journal of Green Energy*, 2013, 10(5), 544-552

Polikovsky M, Fernand F, Sack M, Frey W, Müller G, Golberg A, Towards marine biorefineries: Selective proteins extractions from marine macroalgae *Ulva* with pulsed electric fields. *Innovative Food Science & Emerging Technologies*. 2016

Raso J, Frey W, Ferrari G, Pataro G, Knorr D, Teissie J, Miklavčič D, Recommendations guidelines on the key information to be reported in studies of application of PEF technology in food and biotechnological processes. *Innovative Food Science & Emerging Technologies*, 2016, 37, 312-321

Robic A, Bertrand D, Sassi J F, Lerat Y, Lahaye M, Determination of the chemical composition of ulvan, a cell wall polysaccharide from *Ulva* spp. (Ulvales, Chlorophyta) by FT-IR and chemometrics. *Journal of applied phycology*, 2009, 21(4), 451-456

Rouxel C, Daniel A, Jerome M, Etienne M, Fleurence J. Species identification by SDS-PAGE of red algae used as seafood or a food ingredient. *Food Chem.*, 2001, 74(3), 349-353

Rubinsky B. Irreversible electroporation in medicine. *Technology in Cancer Research & Treatment*, 2007, 6(4), 255-260

Sack M, Eing C, Berghöfer T, Buth L, Stängle R, Frey W, Bluhm H. Electroporation-assisted dewatering as an alternative method for drying plants. *IEEE Transactions on Plasma Science*, 2008, 36(5 PART 3), 2577-2585

Sack M, Bluhm H, New measurement methods for an industrial-scale electroporation facility for sugar beets. *IEEE Trans. Ind. Appl.*, 2008, 44(4), 1074-1083

Sack M, Attmann F, Stängle R, Wolf A, Frey W, Müller G. Upgrade of the electroporation device KEA-MOBIL. *Acta Phys. Pol. A*, 2009, 115(6), 1081-1083

Sack M, Sigler J, Eing C, Stukenbrock L, Stängle R, Wolf A, Müller G. Operation of an electroporation device for grape mash. *IEEE Transactions on Plasma Science*, 2010a, 38(8), 1928-1934

Sack M, Sigler J, Frenzel S, Eing C, Arnold J, Michelberger T, Frey W, Attmann F, Stukenbrock L, Müller G. Research on industrial-scale electroporation devices fostering the extraction of substances from biological tissue. *Food Eng. Rev.*, 2010b, 2(2), 147-156

Stefanidis S D, Heracleous E, Patiaka D T, Kalogiannis K G, Michailof C M, Lappas A A, Optimization of bio-oil yields by demineralization of low quality biomass. *Biomass and Bioenergy*, 2015, 83, 105-115

Tuso P J, Ismail M H, Ha B P, Bartolotto C. Nutritional update for physicians: plant-based diets. *Perm. J.*, 2013, 17(2), 61-6

Vorobiev E, Lebovka N, Pulsed-electric-fields-induced effects in plant tissues: fundamental aspects and perspectives of applications. in: Electrotechnologies for extraction from food plants and biomaterials, *Springer*, 2009, pp. 39-81

Vorobiev E, Lebovka N, Enhanced extraction from solid foods and biosuspensions by pulsed electrical energy. *Food Eng. Rev.*, 2010, 2(2), 95-108

Weaver J C, Chizmadzhev Y A. Theory of electroporation: A review. *Bioelectrochemistry Bioenerg.*, 1996, 41(2), 135-160

Wong K, Chikeung Cheung P. Influence of drying treatment on three Sargassum species 2. Protein extractability, in vitro protein digestibility and amino acid profile of protein concentrates. *J. Appl. Phycol.*, 2001, 13(1), 51-58

Yarmush M L, Golberg A, Serša G, Kotnik T, Miklavčič D. Electroporation-based technologies for medicine: principles, applications, and challenges. *Annu. Rev. Biomed. Eng.*, 2014, 16, 295-320

Zagorulko A, Technological parameters of beet desugaring process by the selective electroplosmolysis. *New Phys. methods foods Process. Moscow Izd. GosINTI*, 1958, 21-27

Zimmermann M B, Iodine deficiency. *Endocrine reviews*, 2009, 30(4), 376-408

What is claimed is:

1. A method for the extraction of a phytochemical from a macroalgae, said method comprising applying pulsed electric field (PEF) treatment to said macroalgae in a solvent, under pressure higher than the ambient pressure, thereby extracting said phytochemical from said macroalgae cells into said solvent,
  wherein the temperature of the solvent during treatment is maintained in the range of 25-90° C.,
  wherein the solvent comprises water and/or an alcohol,
  wherein the phytochemical comprises a protein, peptide, amino acid, phenolic compound, pigment, or a combination thereof, and
  wherein said PEF treatment is characterized by: (i) pulse number of from 1 to about 10,000; (ii) pulse duration of from about 50 ns to about 10 ms; (iii) electric field strength of from about 0.1 to about 100 kV/cm; and (iv) pulse frequency of from 0.1 to about 10000 Hz.

2. The method of claim 1, wherein:
(i) said PEF treatment is non-thermal PEF treatment; or
(ii) said PEF treatment is homogeneously distributed in said solvent; or
(iii) said PEF treatment electroporates the cells of said macroalgae, optionally causing both opening of the membrane of said macroalgae cells and configuration changes in the extracellular matrix of said macroalgae, thus causing extraction of said phytochemical from said macroalgae cells into said solvent; or
(iv) said pressure is from about 1 to about 10 atmospheres; or
(v) said pressure is constant during said PEF treatment, or said pressure varies during said PEF treatment; or
(vi) said solvent is an inorganic solvent selected from the group consisting of fresh water, tap water, saline, and salt water; an alcohol selected from the group consisting of methanol, ethanol, propanol, isopropanol, butanol, t-butyl alcohol, and a combination thereof; or
(vii) the temperature developed in the solvent during said PEF treatment is in a range of 25° C.-70° C.; or
(viii) said macroalgae is dried, semidried or wet macroalgae.

3. The method of claim 1, wherein said phytochemical is a peptide, a protein, a sugar, a small molecule, or a combination thereof.

4. The method of claim 3, wherein said protein is an active site-containing protein, and said PEF treatment does not affect the functional properties of said active site-containing protein.

5. The method of claim 1, further comprising the step of filtering said solvent, after said PEF treatment, thereby removing macroalgae debris from said solvent.

6. The method of claim 1, wherein said PEF treatment is non-thermal PEF treatment; and said phytochemical is a peptide or protein, optionally an active site-containing protein.

7. The method of claim 1, further comprising a step of separating said phytochemical from said solvent.

8. The method of claim 7, wherein said separation is carried out by:
(i) passing said solvent, after said PEF treatment, through a separation column comprising binding means having affinity to said phytochemical, to thereby bind said phytochemical; optionally washing said column to remove unspecific bound molecules; and releasing said phytochemical from said binding means; or
(ii) introducing binding means having affinity to said phytochemical into said solvent either prior to or after said PEF treatment, to thereby bind said phytochemical upon extraction from said macroalgae cells; isolating said binding means after said PEF treatment; and optionally releasing said phytochemical therefrom.

9. The method of claim 8, wherein:
(i) said binding means have functional groups that capable of reversibly interacting with functional groups of said phytochemical; or
(ii) said separation is carried out by introducing binding means having affinity to said phytochemical into said solvent, and said binding means are in the form of beads; or
(iii) said phytochemical is a peptide or protein, and said binding means comprise antibodies; said phytochemical is an enzyme, and said binding means comprise substrates or inhibitors; said phytochemical is a small molecule, and said binding means comprise ionic functional groups that interact with ions of opposite charge of said small molecule; or said phytochemical is a sugar, and said binding means comprise a lectin.

10. The method of claim 1, wherein said macroalgae is submerged in said solvent, and said PEF treatment is carried out in a PEF treatment chamber.

11. The method of claim 10, wherein:
(i) said PEF treatment chamber is a fluidized bed chamber; or
(ii) said PEF treatment chamber is a centrifugal chamber, and wherein said pressure higher than the ambient pressure results from the centrifugal force created by the rotation of said centrifugal chamber during said PEF treatment, and said solvent containing the extracted phytochemical is continuously separated as a result of said centrifugal force.

12. The method of claim 1, wherein the temperature of the solvent during treatment is maintained in the range of 25-60° C.

13. The method of claim 1, wherein said PEF treatment is characterized by: (i) pulse number of from 1 to about 500; (ii) pulse duration of from about 500 ns to about 1 ms; (iii) electric field strength of from about 0.1 to about 10 kV/cm; and (iv) pulse frequency of from 0.1 to about 10 Hz.

* * * * *